(12) United States Patent
Ishida

(10) Patent No.: US 11,439,791 B2
(45) Date of Patent: Sep. 13, 2022

(54) CATHETER AND MANUFACTURING METHOD OF CATHETER

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 189 days.

(21) Appl. No.: 16/529,567

(22) Filed: Aug. 1, 2019

(65) Prior Publication Data
US 2019/0351179 A1 Nov. 21, 2019

Related U.S. Application Data

(63) Continuation of application No. PCT/JP2018/011718, filed on Mar. 23, 2018.

(30) Foreign Application Priority Data

Mar. 23, 2017 (JP) .............................. JP2017-057353

(51) Int. Cl.
*A61M 25/00* (2006.01)
*B29C 48/06* (2019.01)

(52) U.S. Cl.
CPC ...... *A61M 25/0029* (2013.01); *A61M 25/003* (2013.01); *A61M 25/0009* (2013.01);
(Continued)

(58) Field of Classification Search
CPC ...... A61M 2025/0034; A61M 25/0054; A61M 25/003; A61M 25/0026; A61M 25/0028; A61M 25/0029; A61M 2025/0031

See application file for complete search history.

(56) References Cited

U.S. PATENT DOCUMENTS

2004/0064086 A1* 4/2004 Gottlieb ............ A61M 25/0032
604/43
2004/0167463 A1* 8/2004 Zawacki ........... A61M 25/0026
604/43

(Continued)

FOREIGN PATENT DOCUMENTS

JP 2003-320033 A 11/2003
JP 2004-181120 A 7/2004

(Continued)

OTHER PUBLICATIONS

International Searching Authority, "International Search Report," issued in connection with International Patent Application No. PCT/JP2018/011718, dated May 1, 2018.

(Continued)

*Primary Examiner* — Jenna Zhang
(74) *Attorney, Agent, or Firm* — Foley & Lardner LLP

(57) ABSTRACT

A catheter includes: a catheter body defining: a first lumen communicating with a first distal opening, and a second lumen communicating with a second distal opening. The second distal opening is positioned proximal of the first distal opening. A flow path cross-sectional area of the first lumen in at least a part of a distal region of the catheter body that is distal of the second distal opening is larger than a flow path cross-sectional area of the first lumen in a proximal region of the catheter body that is proximal of the second distal opening.

12 Claims, 20 Drawing Sheets

(52) U.S. Cl.
CPC ......... *A61M 25/0074* (2013.01); *B29C 48/06* (2019.02); *A61M 25/0052* (2013.01); *A61M 25/0054* (2013.01); *A61M 25/0097* (2013.01); *A61M 2025/0031* (2013.01); *A61M 2025/0034* (2013.01); *A61M 2025/0037* (2013.01)

(56) References Cited

U.S. PATENT DOCUMENTS

| | | | |
|---|---|---|---|
| 2005/0004554 A1* | 1/2005 | Osborne | A61M 25/0068 604/524 |
| 2005/0085826 A1* | 4/2005 | Nair et al. | A61B 17/221 606/113 |
| 2005/0119597 A1* | 6/2005 | O'Mahony | A61M 25/007 604/4.01 |
| 2009/0240122 A1* | 9/2009 | Avitsian | A61M 25/0023 604/523 |
| 2011/0184266 A1* | 7/2011 | Levin | A61B 5/14532 600/365 |
| 2013/0137977 A1* | 5/2013 | Eder | A61M 2025/0034 604/435 |
| 2017/0273628 A1* | 9/2017 | Ofek | A61B 5/6852 |

FOREIGN PATENT DOCUMENTS

| | | |
|---|---|---|
| JP | 2007-508903 A | 4/2007 |
| JP | 2008-173137 A | 7/2008 |
| JP | 2015-006584 A | 1/2015 |
| JP | 2017-018279 A | 1/2017 |

OTHER PUBLICATIONS

International Searching Authority, "Written Opinion," issued in connection with International Patent Application No. PCT/JP2018/011718, dated May 1, 2018.

International Searching Report and Written Opinion issued in connection with International Patent Application No. PCT/JP2018/011718, dated May 1, 2018.

* cited by examiner

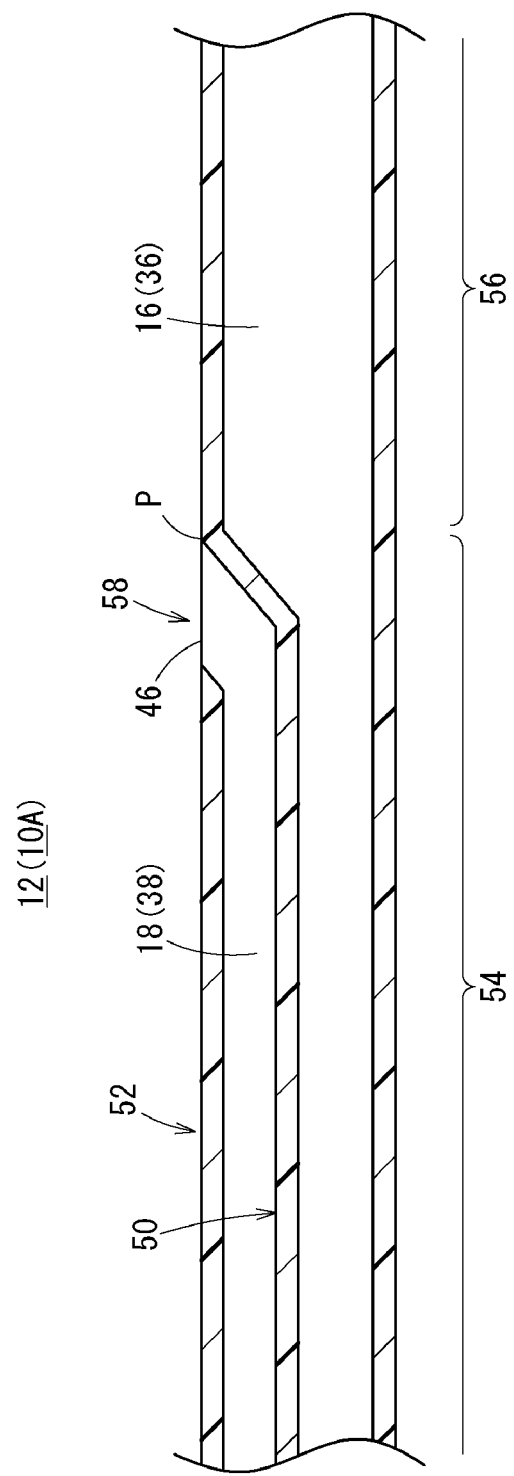

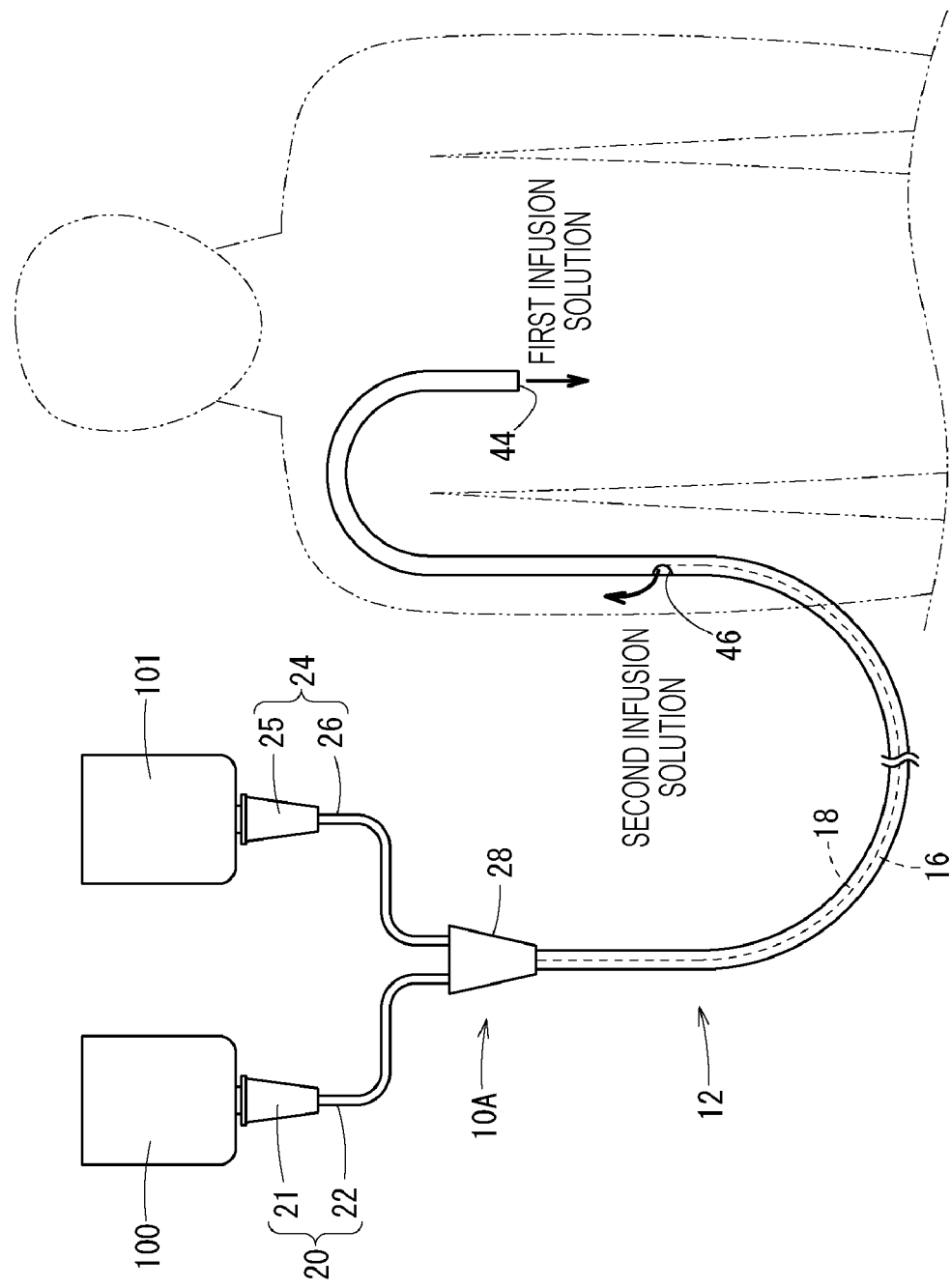

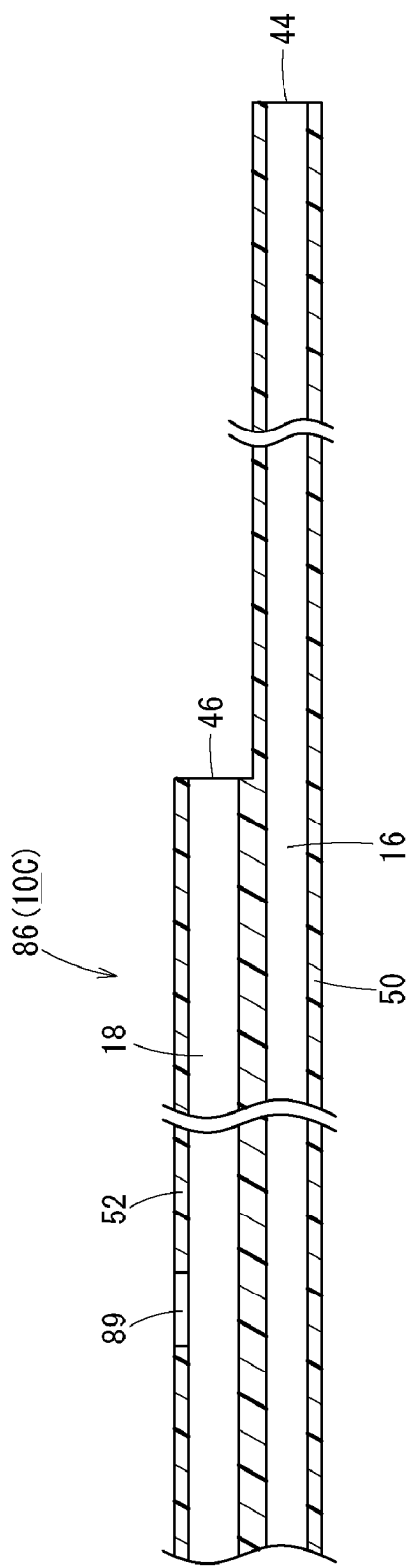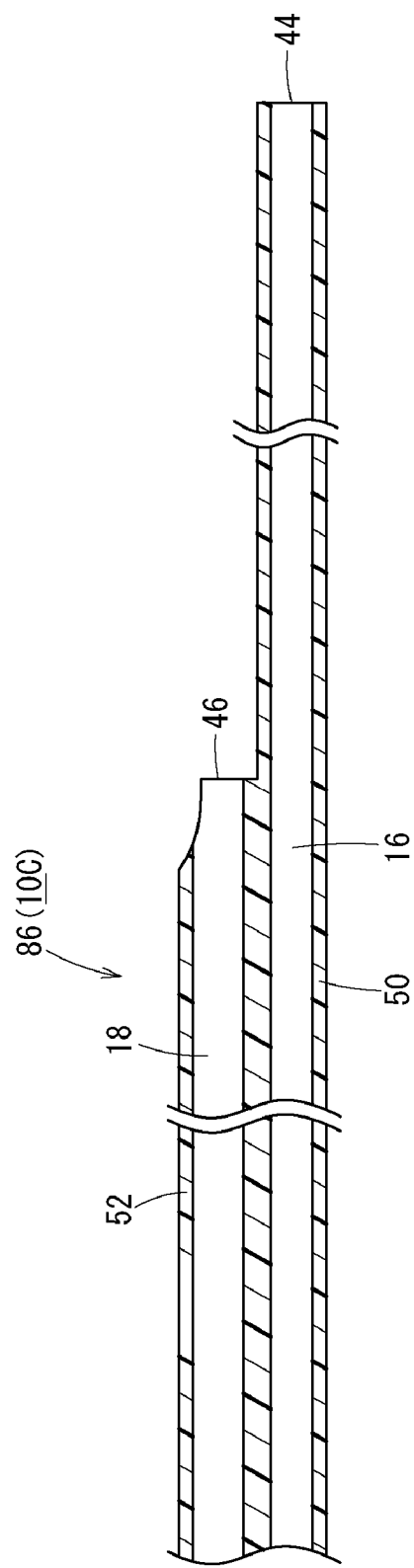

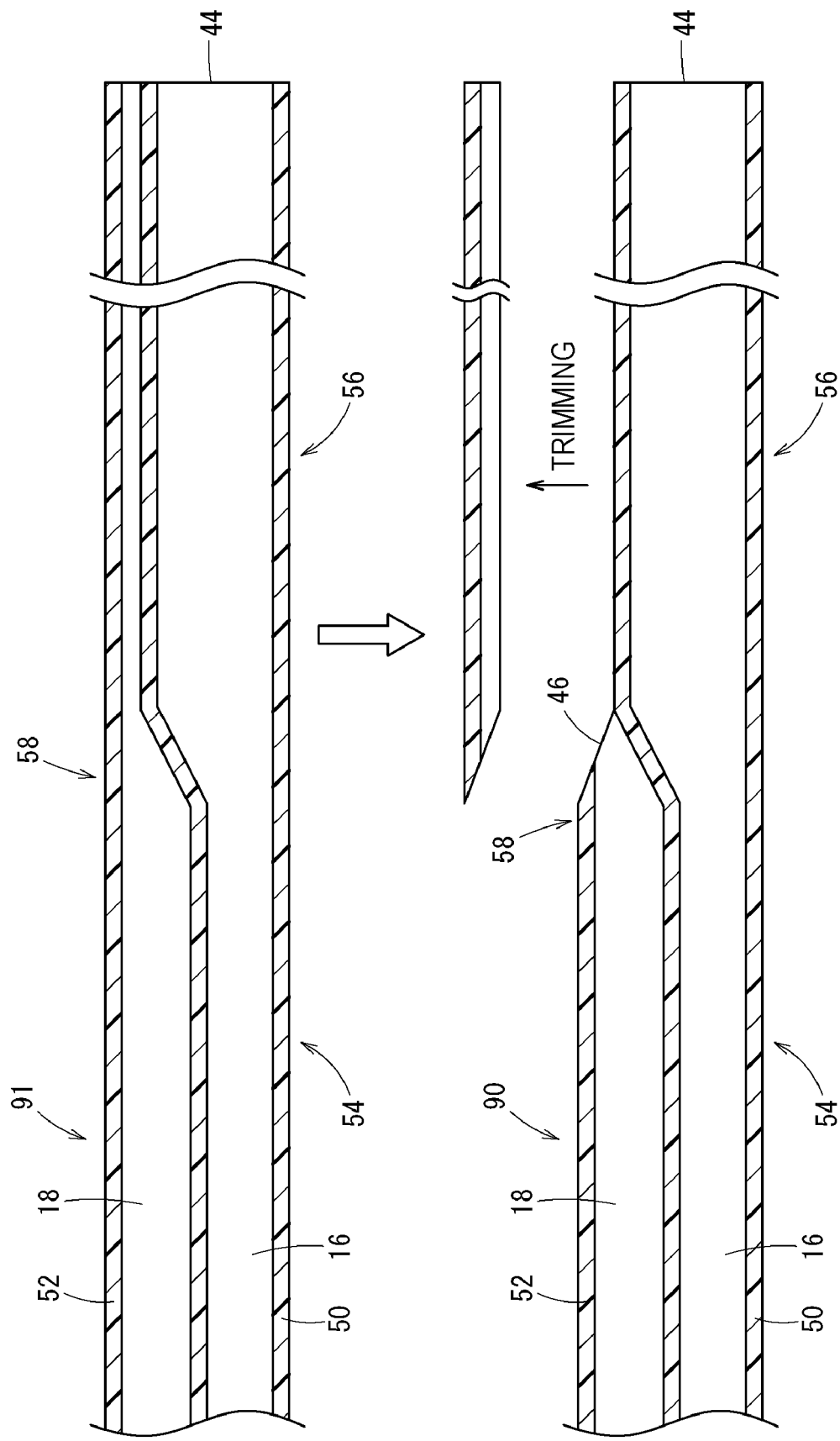

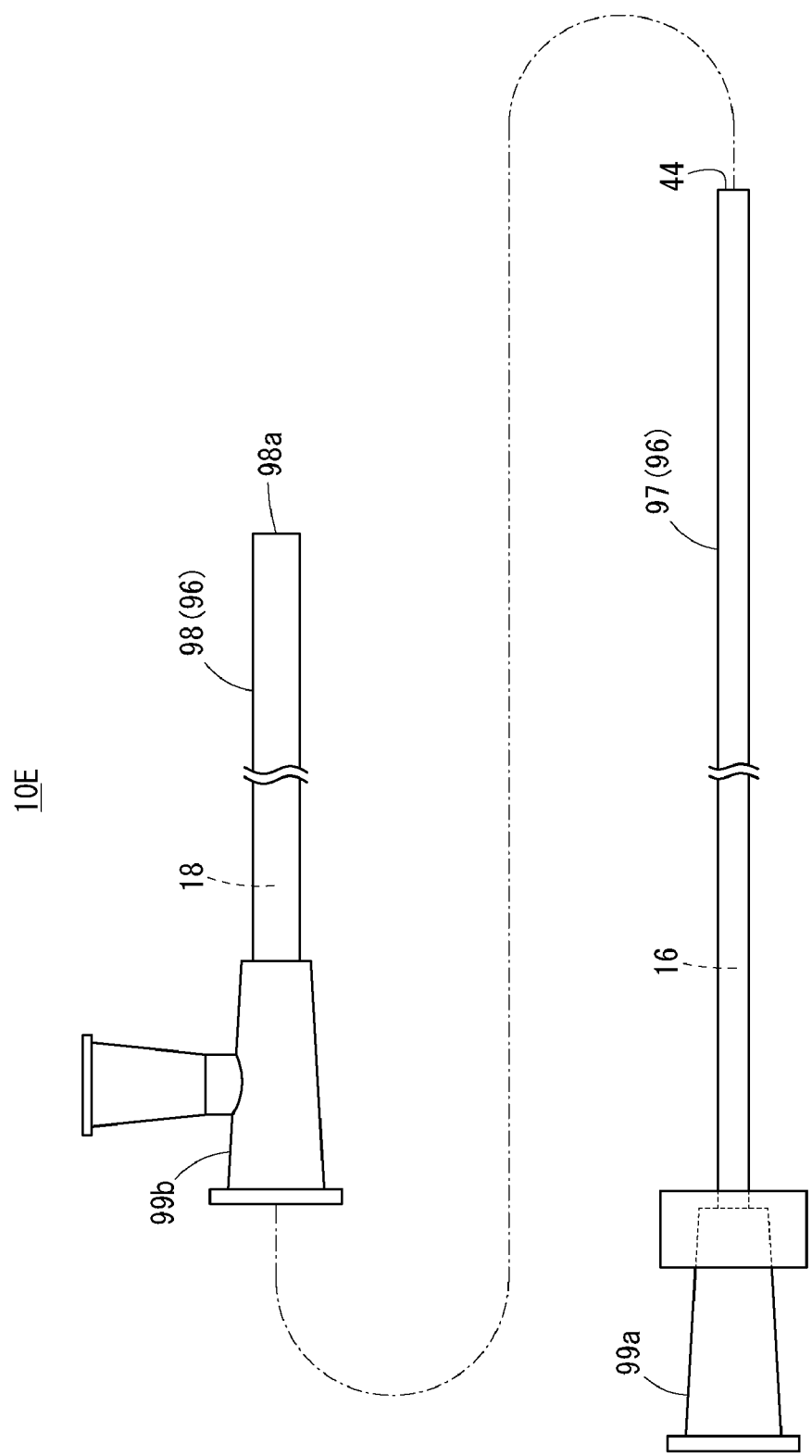

CATHETER AND MANUFACTURING METHOD OF CATHETER

CROSS-REFERENCE TO RELATED APPLICATIONS

This is a bypass continuation of PCT Application No. PCT/JP2018/011718, filed on Mar. 23, 2018, which claims priority to Japanese Application No. 2017-057353, filed on Mar. 23, 2017. The contents of these applications are hereby incorporated by reference in their entireties.

BACKGROUND

The present disclosure relates to a catheter causing a liquid to flow through a plurality of lumens and a manufacturing method of the catheter.

Catheters are used, for example, when performing infusion, transfusion, blood collection, or the like to a patient. Further, a catheter disclosed in JP 2017-18279 A has a plurality of lumens inside a catheter body to be inserted into a patient, each lumen communicating with a distal opening of the catheter body. The catheter configured in this manner is capable of administering different medicines from each distal opening through each lumen.

SUMMARY

It is preferable to administer a highly irritating medicine near a central vein during the infusion to the patient using the catheter, and it is unnecessary to administer a less irritating medicine near the central vein. However, an administration position of one medicine (a target position) needs to be aligned with an administration position of the other medicine when the distal openings of the plurality of lumens are provided on the distal side as described above.

Certain embodiments of the present invention have been made in view of the above circumstances, and one object thereof is to provide a highly versatile catheter capable of realizing various types of treatment by enabling openings of a plurality of lumens to be arranged at appropriate positions with a simple configuration, and a method for manufacturing the catheter.

According to one embodiment, a catheter includes a catheter body having: a first lumen communicating with a first distal opening; and a second lumen provided separately from the first lumen and communicating with a second distal opening. The second distal opening is positioned on a proximal side of the first distal opening. A flow path cross-sectional area of the first lumen is larger than a proximal region on the proximal side of the second distal opening at least in a part of a distal region on a distal side of the second distal opening.

According to the above configuration, the second distal opening is positioned on the proximal side of the first distal opening, and thus, the catheter can realize various types of treatment by arranging the first and second distal openings at appropriate positions, respectively, in a patient's body. For example, it is possible to arrange the second distal opening at a position distant from the central vein and administer a less irritating medicine while arranging the first distal opening near the central vein and administering a highly irritating medicine. Further, the first lumen of the catheter is capable of causing the fluid to stably flow because the flow path cross-sectional area of at least a part of the distal region is larger than the flow path cross-sectional area of the proximal region. That is, because a resistance is small in the distal region even if the resistance increases in the proximal region, a flow rate is secured as a whole, and the fluid is favorably discharged from the first distal opening.

In one aspect, an outer diameter of the proximal region and an outer diameter of the distal region coincide with each other.

As a result, the catheter body can be formed to be thin over the entire length in an axial direction, and can suppress a decrease of a blood flow in a blood vessel when being indwelled in the blood vessel.

In one aspect, the outer diameter of the proximal region is larger than the outer diameter of the distal region.

As a result, the catheter body can easily allow the distal region to enter a deep portion of the body when being inserted by a user.

In one aspect, a cross-sectional shape orthogonal to an axial direction of the first lumen is a non-circular shape in the proximal region and a circular shape in the distal region.

Because the cross-sectional shape of the first lumen in the proximal region is non-circular, the catheter can obtain a sufficient flow path cross-sectional area without increasing the outer diameter of the proximal region.

In one aspect, the catheter body includes a first catheter portion having the first lumen therein, and a second catheter portion having the second lumen therein, and the first catheter portion and the second catheter portion are preferably connected in the proximal region to integrally extend.

Because the first catheter portion and the second catheter portion are connected in the proximal region, the catheter body can be easily manipulated when the user handles the catheter.

In one aspect, the first catheter portion and the second catheter portion are separable along the axial direction of the catheter body.

Because the first catheter portion and the second catheter portion can be separated in the catheter, the separated first catheter portion or second catheter portion can be easily trimmed in accordance with a size of a patient, for example.

In one aspect, a fragile portion that promotes separation is provided at a boundary between the first catheter portion and the second catheter portion.

The fragile portion can further facilitate the separation between the first catheter portion and the second catheter portion, and can suppress unintended breakage or the like of the first and second catheter portions at the time of separation.

In one aspect, the second catheter portion is harder than the first catheter portion.

Because the second catheter portion is harder than the first catheter portion in the catheter, the proximal region can be appropriately hardened to improve the insertability of the catheter body. Further, the distal region remains soft, and thus, can easily follow a blood vessel.

In one aspect, in the state of a tubular body before completion, the catheter body is configured such that an outer circumferential surface is recessed radially inward to form a groove portion, and the groove portion is covered by a covering member.

In one aspect, the catheter body is configured by inserting the first tubular body into the second tubular body before completion.

In one aspect, the catheter body is configured by connecting the first tubular body and the second tubular body before completion.

With each of these configurations, the catheter body has first and second lumens, and is favorably manufactured in the shape in which the flow path cross-sectional area of the first lumen in the distal region is larger than the flow path cross-sectional area of the first lumen in the proximal region.

In another embodiment, a method for manufacturing a catheter that includes a catheter body having: a first lumen communicating with a first distal opening; and a second lumen provided separately from the first lumen and communicating with a second distal opening, the second distal opening positioned on a proximal side of the first distal opening. In the manufacturing method, a molding step of molding a tubular body forming at least a part of the catheter body by extrusion molding is performed, and a molding condition is changed during the molding step to make a flow path cross-sectional area of the first lumen larger in at least a part of a distal region on a distal side of the second distal opening than in a proximal region on the proximal side of the second distal opening.

The catheter and the manufacturing method of the catheter according to certain embodiments of the present invention can allow for various types of treatment and become highly versatile by enabling the arrangement of the openings of the plurality of lumens at the appropriate positions with the simple configuration.

BRIEF DESCRIPTION OF DRAWINGS

FIG. 2 is a side cross-sectional view illustrating a second distal opening of a catheter body of FIG. 1 and a periphery thereof;

FIG. 5 is a schematic view illustrating a method of using the catheter of FIG. 1;

FIG. 13A is a side cross-sectional view illustrating an example of another trim of a catheter, and FIG. 13B is a side cross-sectional view illustrating an example of still another trim of the catheter;

FIG. 14 is a side cross-sectional view for describing a first manufacturing method of the catheter body;

FIG. 20 is a schematic explanatory view illustrating a catheter set of a first tubular body and a second tubular body of FIG. 19.

DETAILED DESCRIPTION

Hereinafter, preferred embodiments (first to fourth embodiments) of a catheter and a manufacturing method of a catheter according to the present invention will be described in detail with reference to the attached drawings.

First Embodiment

Figure 1:
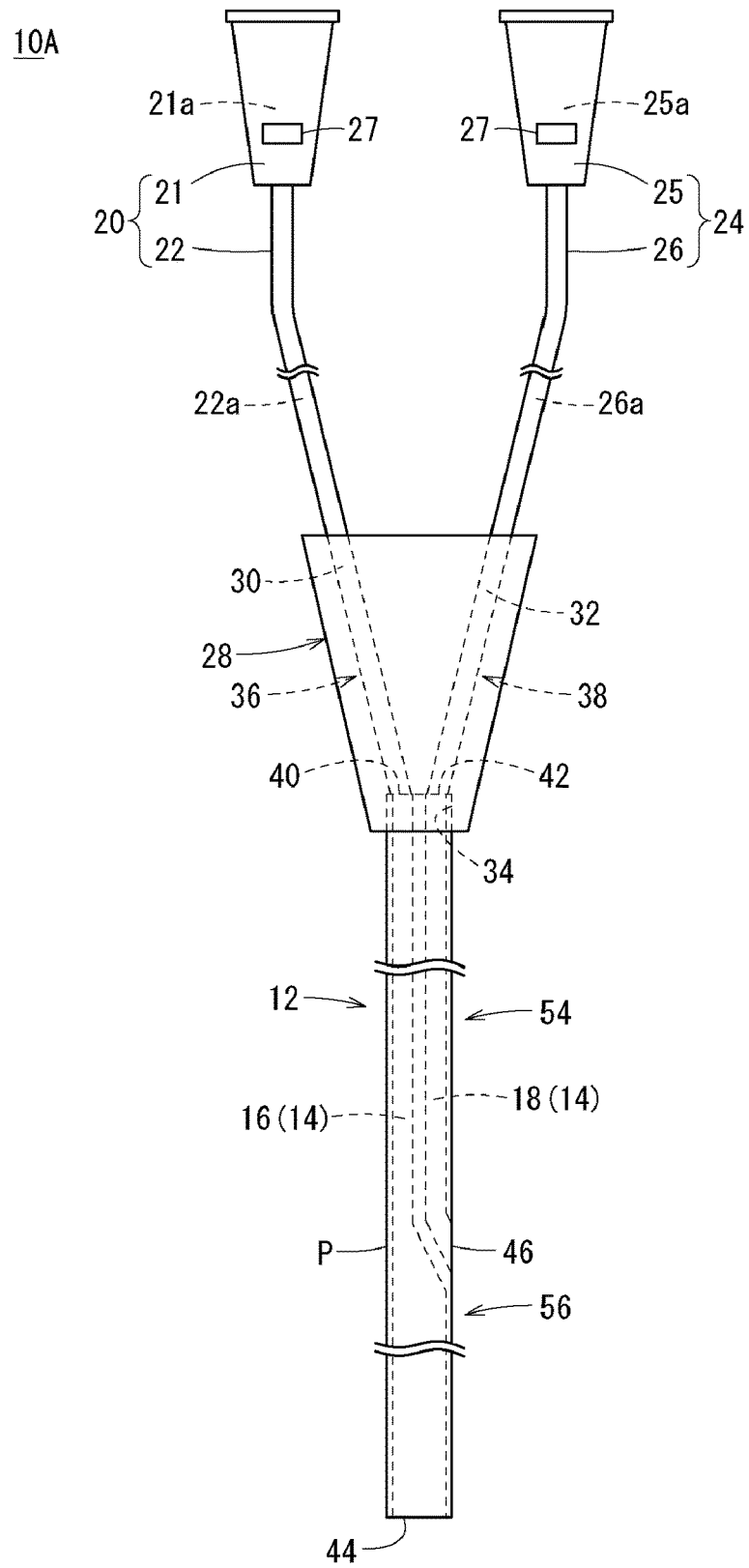
FIG. 1 is a schematic view illustrating a configuration of a catheter according to a first embodiment of the present invention.

A catheter 10A according to a first embodiment of the present invention is configured as a medical device for an infusion line. When the catheter 10A is used, a distal portion side thereof is inserted to indwell in a patient's body, a proximal portion side is connected to a medical bag or the like, thereby causing a fluid such as an infusion solution and blood to flow. Further, the distal portion side from a midway position of the catheter 10A to the patient is formed as a single catheter body 12, and a plurality of lumens 14 are provided in the catheter body 12 as illustrated in FIG. 1. That is, the catheter body 12 is configured as a multi-lumen type, and the catheter 10A can perform administration of different types of infusion solutions, transfusion, blood collection, central venous pressure measurement, and the like using the plurality of lumens 14.

Hereinafter, a description will be given by exemplifying the catheter 10A provided with the double-lumen-type catheter body 12 having two lumens 14 (a first lumen 16 and a second lumen 18) (which is similar in second to fourth embodiments). Incidentally, the catheter body 12 is not limited to the double lumen type, and is applicable to a catheter having three or more lumens with appropriate modifications.

The catheter 10A according to the first embodiment includes a first port 20, a second port 24, a hub 28, and the above-described catheter body 12. The first port 20, the second port 24, and the catheter body 12 are connected to the hub 28, and can be handled integrally as the single catheter 10A.

The first port 20 includes: a first terminal 21 to which a connector of a medical device (not illustrated) such as a medical bag, another catheter, and a syringe is connected at the time of infusion; and a first tube 22 having one end connected to the first terminal 21 and the other end connected to the hub 28. The first terminal 21 is formed in a cylindrical shape having a first hollow portion 21a therein. The first tube 22 is configured as a tubular body that is more flexible than the first terminal 21, and has a first channel 22*a* that communicates with the first hollow portion 21*a* and extends in an axial direction.

Similarly, the second port 24 includes: a second terminal 25 to which a medical device (device different from the device connected the first port 20) (not illustrated), such as a medical bag, another catheter, and a syringe, is connected; and a second tube 26 having one end connected to the second terminal 25 and the other end connected to the hub 28. The second terminal 25 is formed in a cylindrical shape having a second hollow portion 25*a* therein. The second tube 26 is configured as a tubular body similarly to the first tube 22, and has a second channel 26*a* that communicates with the second hollow portion 25*a* and extends in the axial direction.

The first port 20 and the second port 24 may have the same configuration or may have different configurations for connection of mutually different medical devices. For example, lengths of the first tube 22 and the second tube 26 may be different from each other. Further, it may be configured, for example, such that one or both of the first terminal 21 and the second terminal 25 are connected to the hub 28, and no tube is provided. Conversely, one or both of the first port 20 and the second port 24 may have no terminal, and the first tube 22 or the second tube 26 may be directly connected to the medical device. Further, the catheter 10A does not necessarily include one or both of the first and second ports 20 and 24, and the hub 28 may be directly connected to another medical device.

The hub 28 is a block-shaped member having a predetermined thickness and configured for a relay between the first and second ports 20 and 24 described above, and the catheter body 12. The hub 28 is formed to be harder than the catheter body 12, the first tube 22, and the second tube 26, and has a trapezoidal shape in a plan view in which upper bottom side (upper bottom surface) is long and a lower bottom side (lower bottom surface) is short.

A first passage 30 to which the first port 20 (first tube 22) is fixed, and a second passage 32 to which the second port 24 (second tube 26) is fixed are provided inside the hub 28. Further, a mounting hole 34 into which the catheter body 12 is inserted is provided inside the hub 28. The first and second ports 20 and 24 and the catheter body 12 are firmly fixed to the hub 28 by an appropriate fixing method such as vibration welding, high-frequency welding, welding, and adhesion.

The first passage 30 extends into the hub 28 and communicates with the first channel 22*a* of the first tube 22 on the upper bottom side, and communicates with the first lumen 16 of the catheter body 12 fixed to the mounting hole 34 on the lower bottom side. Similarly, the second passage 32 linearly extends inside the hub 28 and communicates with the second channel 26*a* of the second tube 26 on the upper bottom side, and communicates with the second lumen 18 of the catheter body 12 fixed to the mounting hole 34 on the lower bottom side. The first and second passages 30 and 32 have a substantially V-shape inside the hub 28.

Thus, the hub 28 constructs a first path 36 passing through the first port 20, the first passage 30, and the first lumen 16 and a second path 38 passing through the second port 24, the second passage 32, and the second lumen 18 independently (not to communicate with each other). Thus, the catheter 10A can cause a fluid to flow individually through the first and second paths 36 and 38, and flow directions of the fluid in the first and second paths 36 and 38 may be either the same or opposite.

The catheter body 12 connected to the lower bottom side of the hub 28 forms a portion to be inserted into the body from the outside of the patient, and becomes a site where administration of an infusion solution, transfusion, blood collection, central venous pressure measurement, or the like is directly performed with respect to a patient. The catheter body 12 is formed into a tubular body that is relatively long (for example, longer than the first and second tubes 22 and 26).

A total length (axial length) of the catheter body 12 is not particularly limited, but is preferably, for example, in the range of about 100 mm to 2000 mm, and more preferably in the range of 170 mm to 550 mm. Further, the catheter body 12 is formed to have a constant outer diameter along the axial direction. For example, the outer diameter of the catheter body 12 may be designed in the range of about 1 mm to 10 mm.

As illustrated in FIGS. 1 and 2, the first lumen 16 and the second lumen 18 formed in the catheter body 12 extend to be parallel to and not to communicate with each other along the axial direction of the catheter body 12. A first proximal opening 40 communicating with the first lumen 16 and a second proximal opening 42 communicating with the second lumen 18 are provided in a proximal portion of the catheter body 12. The first proximal opening 40 communicates with the first passage 30, and the second proximal opening 42 communicates with the second passage 32, in a fixed state of the catheter body 12 and the hub 28.

Further, the first lumen 16 is configured as a long lumen that is formed over the entire length of the catheter body 12 (a range from a proximal end connected to the hub 28 to a distal end) and has a long axial length. On the other hand, the second lumen 18 is configured as a short lumen that is formed over a range from the proximal end connected to the hub 28 to an axially intermediate position P of the catheter body 12 and has a shorter axial length than the first lumen 16.

Therefore, the catheter body 12 has a first distal opening 44 with which the first lumen 16 communicates at the distal end thereof, and a second distal opening 46 with which the second lumen 18 communicates at the axially intermediate position P. In other words, the second distal opening 46 of the second lumen 18 is positioned on the proximal side of the first distal opening 44 of the first lumen 16.

Hereinafter, a tube portion, which forms the first lumen 16, in the catheter body 12 is also referred to as a first catheter portion 50, and a tube portion forming the second lumen 18 is also referred to as a second catheter portion 52. The first catheter portion 50 and the second catheter portion 52 extend in parallel from the proximal end of the catheter body 12 to the axially intermediate position P, thereby forming a proximal region 54 having a series of tubular outer shapes. That is, the proximal region 54 is a portion where the first catheter portion 50 and the second catheter portion 52 are provided in series. The second catheter portion 52 is not present from the axially intermediate position P to the distal end, thereby forming a distal region 56 where only the first catheter portion 50 extends.

In the catheter body 12 according to the first embodiment, outer diameters of the proximal region 54 and the distal region 56 are set to be substantially constant. Thus, in the first lumen 16, a flow path cross-sectional area Sd of the distal region 56 where the second lumen 18 is not present is larger than a flow path cross-sectional area Sp of the proximal region 54 where the second lumens 18 overlaps the first lumen 16.

Further, it is preferable that a total length of the first lumen 16 and a total length of the second lumen 18 be appropriately designed in accordance with a patient to which the catheter 10A is applied. One example is to provide different dimensions for children and adults. For example, for children, the total length of the first catheter portion 50 (the first lumen 16) is preferably in the range of 170 mm to 280 mm, and the total length of the second catheter portion 52 (the second lumen 18) is preferably in the range of 40 mm to 60 mm. Further, for adults, the total length of the first catheter portion 50 is preferably in the range of 350 mm to 550 mm, and the total length of the second catheter portion 52 is preferably in the range of 80 mm to 120 mm. In other words, a ratio of the total length of the second catheter portion 52 relative to the first catheter portion 50 is preferably 0.15 to 0.34.

Further, a transition region 58 is provided at the axially intermediate position P of the catheter body 12 so as to gradually increase a flow path cross-sectional area S1 of the first lumen 16 in a distal direction. That is, the proximal region 54 and the distal region 56 intersect each other in the transition region 58. A distal side of the second lumen 18 is bent obliquely in the transition region 58 in accordance with a change in the outer diameter of the first catheter portion 50 and is connected to the second distal opening 46 provided on the outer circumferential surface of the catheter body 12.

Figure 3A:
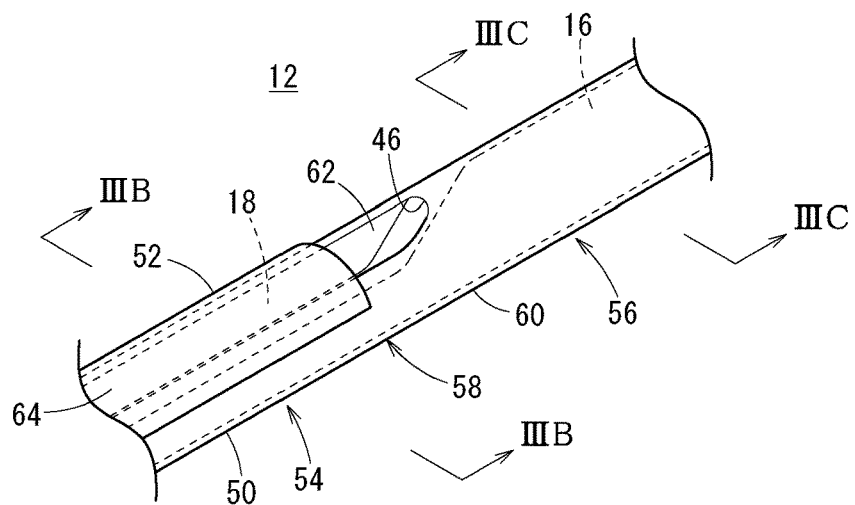
FIG. 3A is a perspective view illustrating a second distal opening of the catheter body of FIG. 1 and a periphery thereof.
Figure 3B:
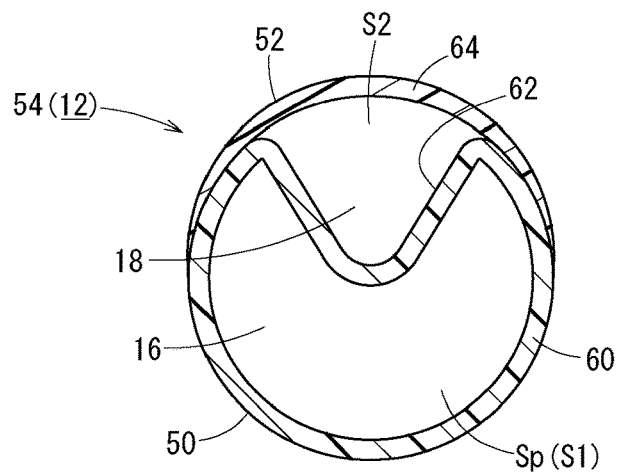
FIG. 3B is a cross-sectional view taken along line IIIB-IIIB of FIG. 3A.
Figure 3C:
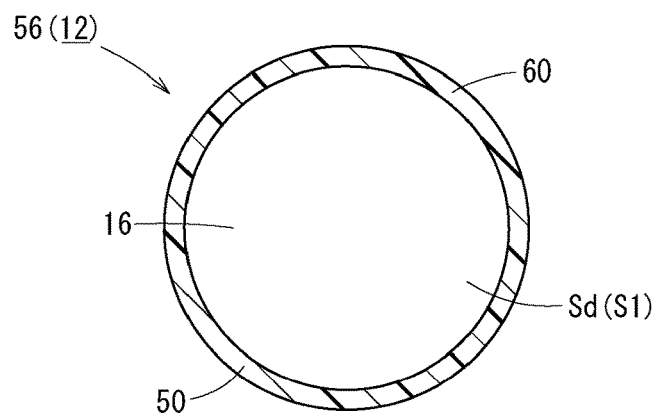
FIG. 3C is a cross-sectional view taken along line IIIC-IIIC of FIG. 3A.

The above catheter body 12 can be manufactured by forming a groove portion 62 on an outer circumferential surface of a tubular body 60 before completion, which has been molded by extrusion molding, and covering the groove portion 62 with a resin sheet 64 (covering member), for example, as illustrated in FIGS. 3A to 3C. That is, a lumen extending inside the tubular body 60 corresponds to the first lumen 16, and the groove portion 62 corresponds to the second lumen 18 in the completed state of the catheter body 12.

Thus, the first lumen 16 of the proximal region 54 is formed in a substantially crescent shape (a C-shape: a non-circular shape) and extends in the axial direction in a cross-sectional view orthogonal to the axial direction. On the other hand, the first lumen 16 of the distal region 56 is formed in a circular shape. Therefore, the flow path cross-sectional area Sd of the distal region 56 becomes larger than the flow path cross-sectional area Sp of the proximal region 54. Further, the cross-sectional shape of the first lumen 16 is gradually changed from the crescent shape to the circular shape in the transition region 58.

On the other hand, a flow path cross-sectional area of the second lumen 18 is set in accordance with a recessed degree of the outer circumferential surface of the tubular body 60. The flow path cross-sectional area Sp (S1) of the first lumen 16 in the proximal region 54 is set to be larger than the flow path cross-sectional area S2 of the second lumen (S1>S2). Incidentally, a relationship between the flow path cross-sectional area S1 of the first lumen 16 and the flow path cross-sectional area S2 of the second lumen 18 is not particularly limited, and may be configured such that the relationship of S1=S2 or S1<S2 is established by, for example, forming the first lumen 16 in a semicircular shape or forming the groove portions 62 to be large.

Figure 4:
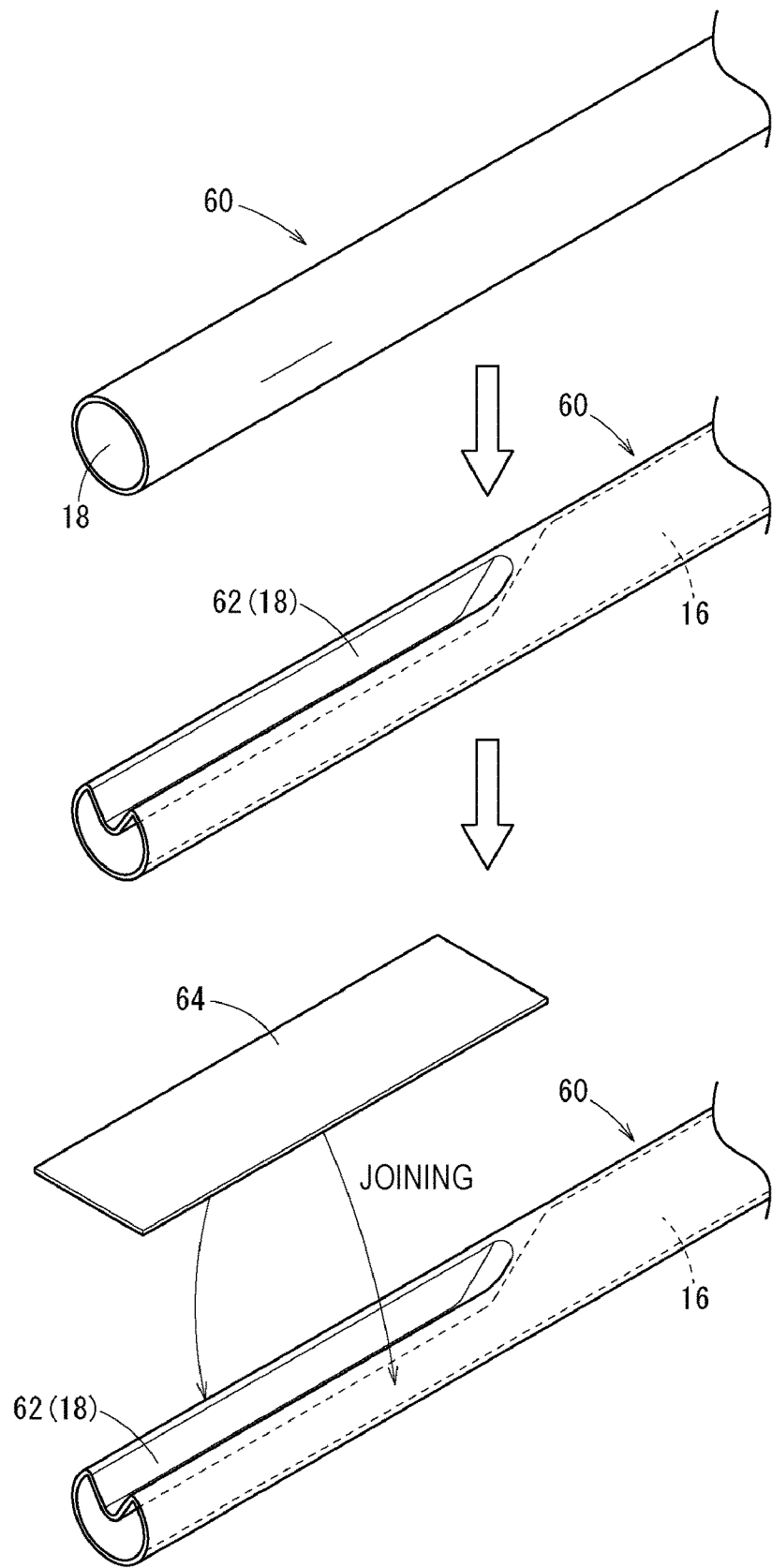
FIG. 4 is an explanatory view illustrating a manufacturing process of the catheter body of FIG. 1.

When manufacturing the above-described catheter body 12, first, the tubular body 60 is manufactured by extrusion molding or the like (a molding step) as illustrated in FIG. 4. Next, groove processing (thermal processing) is performed as secondary processing on a range corresponding to the proximal region 54 of the tubular body 60 so as to recess the outer circumferential surface of the tubular body 60, thereby forming the groove portion 62 (a groove portion formation step). As a result, the lumen inside the tubular body 60 becomes the shape of the first lumen 16 (the proximal region 54 is the non-circular shape and the distal region 56 is the circular shape).

Then, the groove portion 62 is covered with the resin sheet 64 manufactured separately, and the resin sheet 64 and the outer circumferential surface of the tubular body 60 are fixed (a proximal region formation step). Examples of a fixing means include fusion by heat, ultrasound, or the like, joining by a solvent or an adhesive, and the like. As a result, the resin sheet 64 is liquid-tightly fixed to the tubular body 60, and the second lumen 18 is formed. Further, processing is performed so as to reduce a step between an end of the resin sheet 64 and the tubular body 60 at the time of fixing in the proximal region formation step. When the step slightly remains, it is desirable to eliminate the step by coating so as to include at least such a step portion.

Further, it is preferable that the catheter body 12 (the tubular body 60 and the resin sheet 64) be configured to appropriately have flexibility (pliability) so as to be capable of following a blood vessel of a patient and stiffness (rigidity) so as not to be crushed by the blood vessel. Although not particularly limited, examples of materials forming the catheter body 12 include a polyolefin-based resin such as high-density polyethylene, polypropylene, polybutene, vinyl chloride, and an ethylene-vinyl acetate copolymer, or a polyolefin-based elastomer thereof, a fluorine-based resin or a fluorine-based elastomer, a methacrylic resin, polyphenylene oxide, modified polyphenylene ether, polyethylene terephthalate, polybutylene terephthalate, polyether ether ketone, polyamide imide, polyether imide, polyether sulfone, cyclic polyolefin, a polyurethane elastomer, a polyester elastomer, polyamide or a polyamide elastomer, polycarbonate, polyacetal, a styrene resin or a styrene-based elastomer, thermoplastic polyimide, and the like.

Incidentally, it is likely to be difficult to distinguish the first port 20 (the first path 36) and the second port 24 (the second path 38) in the above catheter 10A in a state where the catheter body 12 has been inserted into the patient. Thus, it is preferable that the catheter 10A be provided with a display unit 27 that enables the first path 36 and the second path 38 to be recognized as illustrated in FIG. 1. The display unit 27 may be provided in any of the first and second ports 20 and 24, the hub 28, and the catheter body 12 (the first and second catheter portions 50 and 52). For example, it is preferable to display a fact that an infusion solution is administered to a central vein, that it is connected to the long lumen, that it is non-pressure-resistant (see the third embodiment), a flow rate, or the like on the display unit 27 provided in the first terminal 21 and the first tube 22. Further, it is preferable to display that an infusion solution is administered to an arm, that it is connected to the short lumen, that it is pressure-resistant (see the third embodiment), a flow rate, or the like, for example, on the display unit 27 provided to the second terminal 25 and the second tube 26.

The catheter 10A according to the first embodiment is basically configured as described above, and a use method and effects thereof will be described hereinafter. The catheter 10A is used at the time of infusion and transfusion, and the catheter body 12 is inserted to indwell in a patient's blood vessel using the same method as a central venous catheter (the Seldinger method, the modified Seldinger method, a direct puncture method, or the like). At the time of insertion, a user can easily manipulate the catheter body 12 using the proximal region 54 where the first catheter portion 50 and the second catheter portion 52 are connected. Incidentally, the catheter 10A may be inserted to indwell using a catheter assembly having an inner needle in the same manner as an indwelling needle and a mid-line catheter.

In the indwelling state of the catheter body 12 as illustrated in FIG. 5, the second distal opening 46 of the second lumen 18 is arranged at a position distant from the central vein (for example, in the arm of the patient), and the first distal opening 44 of the first lumen 16 is arranged near the central vein. In particular, as portions being inserted into the patient, it is preferable that the second lumen 18 be positioned outside (a shoulder side of the patient) distant from the central vein and that the first lumen 16 be arranged inside (an armpit side of the patient) near the central vein. With this arrangement, in the catheter body 12 that is curved in the blood vessel, the second distal opening 46 hardly contacts a wall of the blood vessel so that it is possible to favorably perform the administration of the infusion solution.

Incidentally, it is preferable that circumferential positions of the hub 28 and the first and second lumens 16 and 18 be properly designed in the catheter 10A so as to stably obtain the above-described arrangement. It is a matter of course that, as the portions of the catheter body 12 that is inserted into the patient, the first lumen 16 can be positioned outside the first lumen 16 distant from the central vein, and the second lumen 18 can be arranged on the inside close to the central vein. Further, it may be configured such that the first lumen 16 and the second lumen 18 are arranged at substantially the same distance with respect to the central vein (arranged in parallel to the patient's skin). As a result, the catheter body 12 can easily follow a curvature of the blood vessel.

Further, when the catheter body 12 is set to a length that allows the distal region 56 to be positioned in a curved blood vessel near the shoulder during indwelling, it is possible to reduce mechanical stimulation, caused by the catheter 10A, on the curved blood vessel near the shoulder.

Along with the indwelling of the catheter body 12, a medical bag 100 storing a first infusion solution is connected to the first port 20 of the catheter 10A. Therefore, the first infusion solution is administered near the central vein through the first channel 22a of the first port 20, the first passage 30 of the hub 28, and the first lumen 16 of the catheter body 12. Although the first infusion solution receives a great resistance in the proximal region 54 at the time of flowing in the first lumen 16, the resistance decreases in the distal region 56, and the flow rate increases as compared with a case where the distal region 56 of the first lumen 16 has the same flow path cross-sectional area as the proximal region 54 of the first lumen 16.

On the other hand, a medical bag 101 storing a second infusion solution, which is less irritating than the first infusion solution, is connected to the second port 24 of the catheter 10A. Therefore, the second infusion solution is administered at a position distant from the central vein through the second channel 26a of the second port 24, the second passage 32 of the hub 28, and the second lumen 18 of the catheter body 12. As described above, the second lumen 18 is curved in a tapered shape by the transition region 58 near the second distal opening 46. Thus, the second infusion solution having flown through the second lumen 18 is smoothly discharged toward a side of the catheter body 12 from the second distal opening 46.

That is, the catheter 10A in the indwelling state enables the highly irritating first infusion solution to be favorably administered from the first distal opening 44 arranged near the central vein, and the less irritating second infusion solution to be favorably administered from the second distal opening 46 arranged at the position distant from the central vein. Further, the second lumen 18 has the short axial length, and thus, is suitable for collection of patient's blood, and it is possible to suppress hemolysis at the time of blood collection. Because the proximal region 54 of the catheter body 12 is thin, it is possible to suppress the stimulation on the blood vessel and to suppress generation of a thrombus without blocking the blood flow.

As described above, the second distal opening 46 is positioned on the proximal side of the first distal opening 44 in the catheter 10A according to the first embodiment. Thus, various types of treatment can be realized by arranging the first and second distal openings 44 and 46 at appropriate positions in the patient's body. Further, the flow path cross-sectional area Sd of the distal region 56 is larger than the flow path cross-sectional area Sp of the proximal region 54 in the first lumen 16 of the catheter 10A so that the flow rate as the entire lumen is secured. Accordingly, the fluid flows stably, and is favorably discharged from the first distal opening 44.

Further, because the outer diameter of the proximal region 54 and the outer diameter of the distal region 56 coincide with each other, the catheter body 12 can be formed to be thin over the entire axial length, and it is possible to suppress a decrease of the amount of blood flow in the blood vessel at the time of indwelling in the blood vessel. Further, the cross-sectional shape of the first lumen 16 in the proximal region 54 is non-circular, the catheter 10A can obtain the sufficient flow path cross-sectional area Sp without increasing the outer diameter of the proximal region 54.

Incidentally, the catheter 10A is not limited to the above-described configuration, and it is a matter of course that various modifications and applications can be made. For example, the first and second lumens 16, 18 may be freely designed in terms of the cross-sectional shape. In particular, the first lumen 16 is not particularly limited in terms of the shape as long as the flow path cross-sectional area Sd of at least a part of the distal region 56 is larger than the flow path cross-sectional area Sp of the proximal region 54.

Further, for example, the second distal opening 46 is provided at an opposite position (a position different by 180° in the circumferential direction) at a location connected to the first catheter portion 50 of the second catheter portion 52 in the above-described catheter body 12. However, the position of the second distal opening 46 on the circumferential direction of the catheter body 12 is not limited, and may be provided at, for example, a position shifted by 90° in the circumferential direction from the connection location.

Figure 6A:
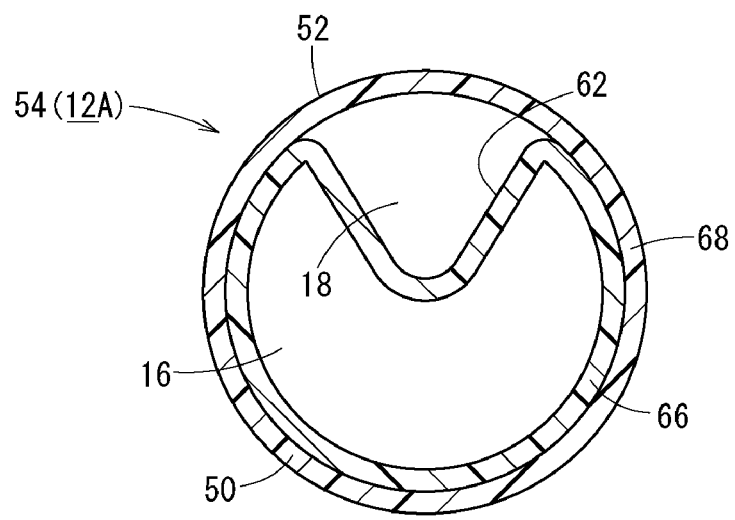
FIG. 6A is a cross-sectional view of a catheter body according to a first configuration example.

Further, a catheter body 12A according to a first configuration example illustrated in FIG. 6A is different from the catheter body 12 in terms that the entire outer circumferential surface of a first tubular body 66 having the groove portion 62 in the proximal region 54 is accommodated in a second tubular body 68 that is slightly larger. The second tubular body 68 forms a part of the second catheter portion 52, and has a shorter axial length than the first catheter portion 50. Further, the first tubular body 66 is formed such that the flow path cross-sectional area Sd of the distal region 56 of the first lumen 16 is larger than the flow path cross-sectional area Sp of the proximal region 54, which is similar to the first catheter portion 50 of the first embodiment.

An outer circumferential surface of the first tubular body 66 and an inner circumferential surface of the second tubular body 68 are joined by an appropriate fixing method except for the groove portion 62. As a result, the groove portion 62 covered by the second tubular body 68 forms the second lumen 18 so that a fluid can flow smoothly. Incidentally, even if the first tubular body 66 and the second tubular body 68 are not joined, it is possible to cause the fluid to flow via a gap therebetween.

Figure 6B:
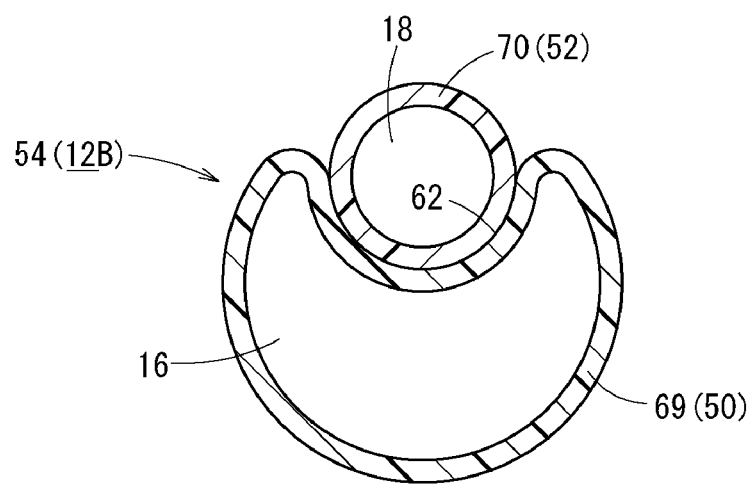
FIG. 6B is a cross-sectional view of a catheter body according to a second configuration example.

A catheter body 12B according to a second configuration example illustrated in FIG. 6B is different from the catheter bodies 12 and 12A in terms that another tube having the second lumen 18 is arranged in the groove portion 62 of a circular tubular body in the proximal region 54. That is, the tubular body 69 before the manufacturing the catheter body 12B forms the first catheter portion 50, and another tube 70 arranged in the groove forms the second catheter portion 52.

The tube 70 has a shorter axial length than the first catheter portion 50, and is joined to an outer circumferential surface forming the groove portion 62 of the tubular body 69 by an appropriate fixing means in the state of being arranged in the groove portion 62. Further, the tubular body 69 is formed such that the flow path cross-sectional area Sd of the distal region 56 of the first lumen 16 is larger than the flow path cross-sectional area Sp of the proximal region 54, which is similar to the first embodiment. As a result, the first lumen 16 and the second lumen 18 can cause a fluid to flow smoothly. Incidentally, the tube 70 may be non-circular, and an outer shape of the proximal region 54 may be circular.

Second Embodiment

Figure 7:
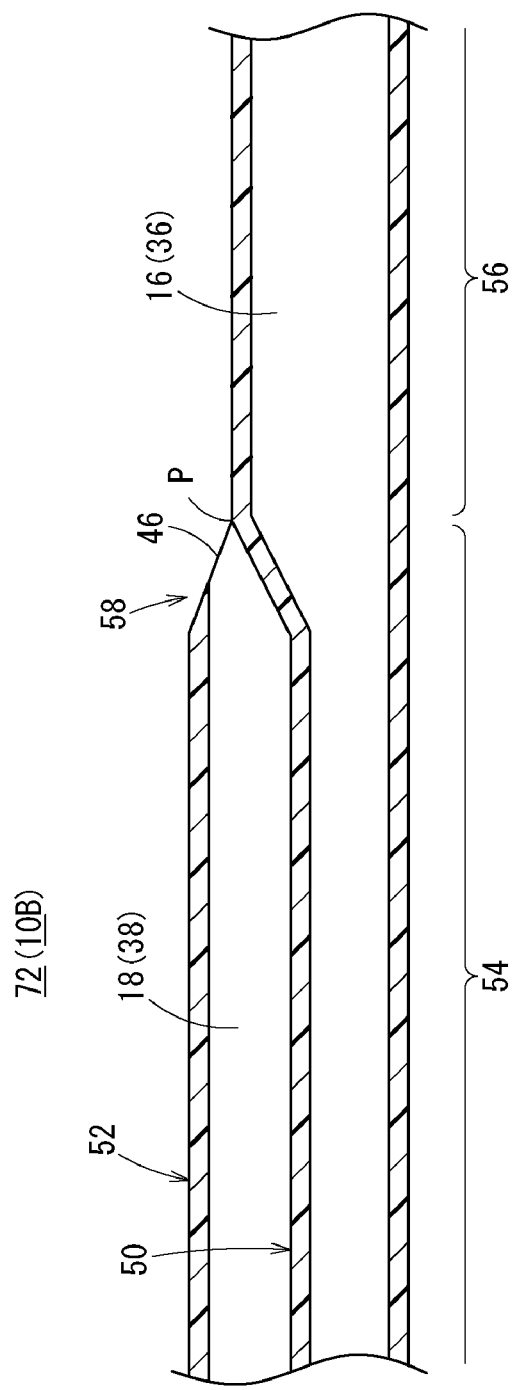
FIG. 7 is a side cross-sectional view illustrating a second distal opening of a catheter body of a catheter according to a second embodiment and a periphery thereof.

A catheter 10B according to the second embodiment is different from the catheter 10A according to the first embodiment in terms that the proximal region 54 of a catheter body 72 is formed to be slightly thicker than the distal region 56 as illustrated in FIG. 7. Incidentally, in the following description, the same configurations or configurations having the same functions as those in the first embodiment will be denoted by the same reference signs, and detailed descriptions thereof will be omitted.

Specifically, the catheter body 72 is configured as a tubular body in which the first catheter portion 50 and the second catheter portion 52 are connected in series by extrusion molding or the like. Incidentally, the catheter body 72 is not limited to this configuration, and, for example, may have a structure in which the groove portion 62 is provided in the tubular body 60, and the groove portion 62 is covered with a covering member or a tube is arranged similarly to the first embodiment.

Figure 8A:
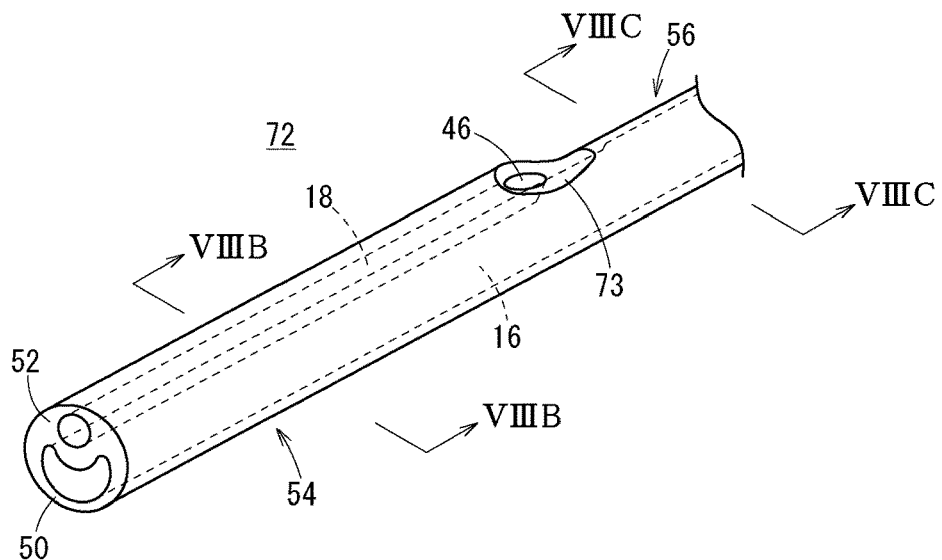
FIG. 8A is a perspective view illustrating the second distal opening of the catheter body of FIG. 7 and the periphery thereof.

An outer circumferential surface, near a location where the first lumen 16 is formed, in a circumferential direction of the catheter body 72 is continuous with the proximal region 54 and the distal region 56 without any change in outer diameter. On the other hand, an outer circumferential surface near a location where the second lumen 18 is formed has a tapered surface 73, which gradually becomes thinner in the transition region 58, and an outer diameter changes from the large-diameter proximal region 54 to the small-diameter distal region 56 as illustrated in FIGS. 7 and 8A.

Figure 8B:
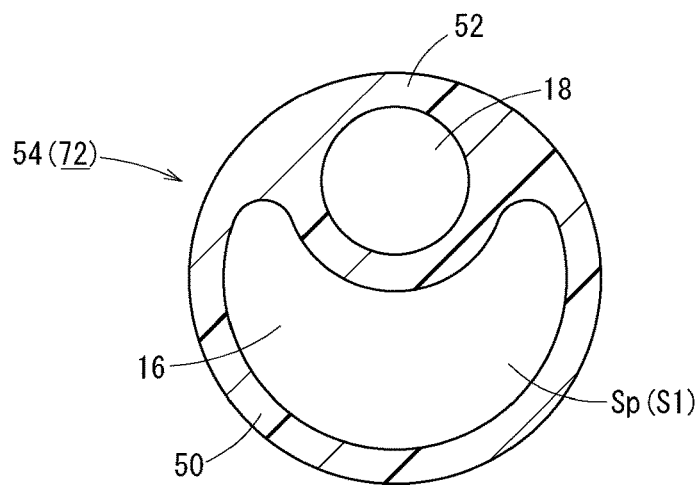
FIG. 8B is a cross-sectional view taken along line VIIIB-VIIIB of FIG. 8A.
Figure 8C:
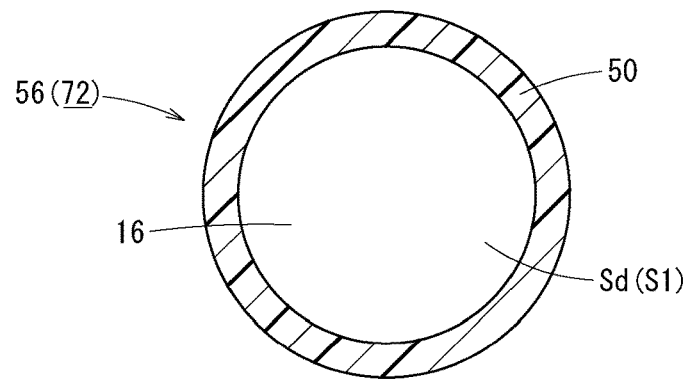
FIG. 8C is a cross-sectional view taken along line VIIIC-VIIIC of FIG. 8A.

Further, the proximal region 54 of the catheter body 72 has a large outer diameter so that a diameter of one or both of the first and second lumens 16 and 18 in the proximal region 54 can be increased to secure a flow rate of a fluid. In the first lumen 16, a cross-sectional shape of the proximal region 54 is formed in a crescent shape (non-circular shape), and a cross-sectional shape of the distal region 56 is formed in a circular shape as illustrated in FIGS. 8B and 8C. Thus, the first lumen 16 has the relationship that the flow path cross-sectional area Sp of the proximal region 54<the flow path cross-sectional area Sd of the distal region 56, which is similar to the first embodiment.

On the other hand, the second lumen 18 extends inside the proximal region 54 with a constant diameter, and communicates with the second distal opening 46 formed in the above-described tapered surface 73. Further, a wall partitioning the first lumen 16 and the second lumen 18 in the transition region 58 is inclined radially outward together with a formation position of the second distal opening 46, the second lumen 18 can discharge the fluid obliquely forward.

As described above, the catheter 10B according to the second embodiment can obtain the same effects as the catheter 10A according to the first embodiment. In particular, the proximal region 54 is thicker than the distal region 56 of the catheter body 72, and thus, the catheter 10B can ensure the sufficient flow rate in the first and second lumens 16 and 18 so that the treatment using the catheter 10B can be favorably performed. Further, the proximal region 54 favorably supports the distal region 56 when the catheter body 72 is inserted by a user so that the distal region 56 can easily enter a deep portion of the body.

Third Embodiment

Figure 9:
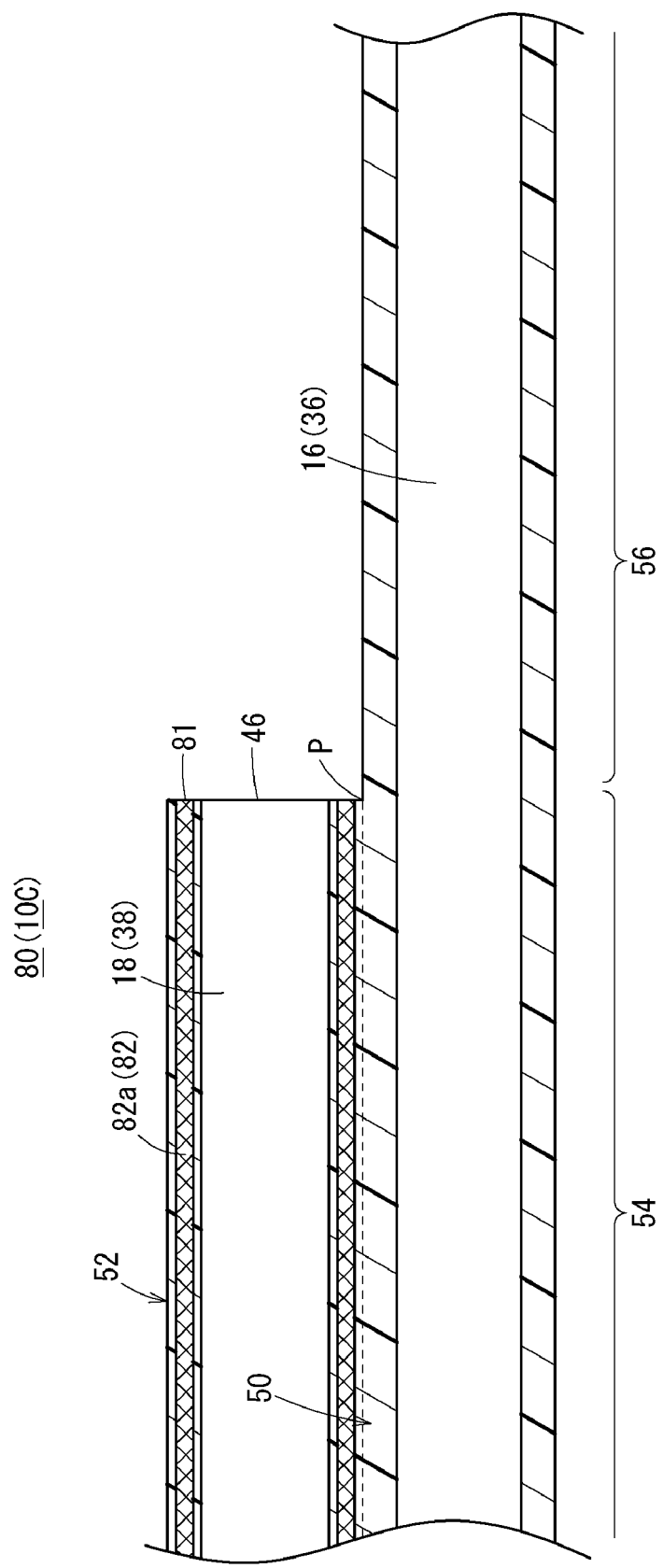
FIG. 9 is a side cross-sectional view illustrating a second distal opening of a catheter body of a catheter according to a third embodiment and a periphery thereof.

A catheter 10C according to the third embodiment is different from the catheters 10A and 10B according to the first and second embodiments in terms that the flow path cross-sectional area S1 of the first lumen 16 of a catheter body 80 extends without any change between the proximal region 54 and the distal region 56 as illustrated in FIG. 9. That is, the first lumen 16 is configured such that the flow path cross-sectional area Sp of the proximal region 54=the flow path cross-sectional area Sd of the distal region 56.

Specifically, the catheter body 80 is configured as a tubular body in which the first catheter portion 50 and the second catheter portion 52 are connected in series by extrusion molding or the like. Further, the first lumen 16 and the second lumen 18 extend in parallel in the proximal region 54, but only the first lumen 16 still extends in the distal region 56.

Therefore, an outer shape of the proximal region 54 of the catheter body 80 is thicker than an outer shape of the distal region 56, and the axially intermediate position P at which the proximal region 54 and the distal region 56 switch is set at a step portion 81 whose outer diameter changes. The second distal opening 46 of the second lumen 18 is formed in the step portion 81 to face a distal direction along an axial direction of the second lumen 18.

Here, the catheter body 80 according to the third embodiment is configured such that a pressure resistance (rigidity) of the second catheter portion 52 is higher than a pressure resistance of the first catheter portion 50. That is, the second catheter portion 52 has a pressure-resistant structure 82, and the first catheter portion 50 has a non-pressure-resistant structure (not illustrated) (does not have the pressure-resistant structure 82).

Specifically, the pressure-resistant structure 82 is realized by providing a reinforcing layer 82a inside the second catheter portion 52. The reinforcing layer 82a can be made of, for example, a coiled or meshed metal wire (so-called blade), or can be made of a material harder than an inner layer or an outer layer. Further, for example, for the pressure-resistant structure 82 and the non-pressure-resistant structure, the second catheter portion 52 may be molded using a hard material (for example, hard polyurethane), and the first catheter portion 50 may be molded using a material (for example, soft polyurethane) softer than the material of the second catheter portion 52. Further, for example, the pressure-resistant structure 82 and the non-pressure-resistant structure can also be realized by molding the second catheter portion 52 to be thick and molding the first catheter portion 50 to be thin.

That is, because the second catheter portion 52 has the pressure-resistant structure 82 in the catheter body 80, the pressure resistance of the proximal region 54 can be significantly improved. The pressure resistance of the second catheter portion 52 is preferably 325 PSI or more.

Further, because the first catheter portion 50 has the non-pressure-resistant structure, the distal region 56 becomes flexible, and the distal region 56 can be made to follow a blood vessel easily in an indwelling state. Moreover, the reinforcing layer 82a provided only in the second catheter portion 52 can suppress an excessively increase in entire rigidity of the catheter body 80.

Incidentally, the catheter body 80 may be configured such that the first catheter portion 50 has the pressure-resistant structure 82, and the second lumen 18 has a non-pressure-resistant structure. Further, when configured to have three or more lumens 14, the catheter body 80 may have a structure having one catheter portion (one lumen) having the pressure-resistant structure 82. In particular, by setting the lumen having a large diameter among the plurality of lumens 14 to have the pressure-resistant structure 82, the rigidity and flexibility of the whole catheter body 80 can be properly distributed.

Hereinafter, a description will be given regarding several other modifications, made along a gist of the present invention, for the catheters 10A to 10C (the catheter bodies 12, 12A, 12B, 72, and 80) according to the present invention (the first to third embodiments). Incidentally, in the following description, constituent parts modified with the catheter 10C according to the third embodiment (the catheter body 80 in which the flow path cross-sectional area S1 of the first lumen 16 is constant along the axial direction) as a basic structure will be described. It is a matter of course that the following modifications can also be applied to the catheters 10A and 10B according to the first and second embodiments.

Figure 10:
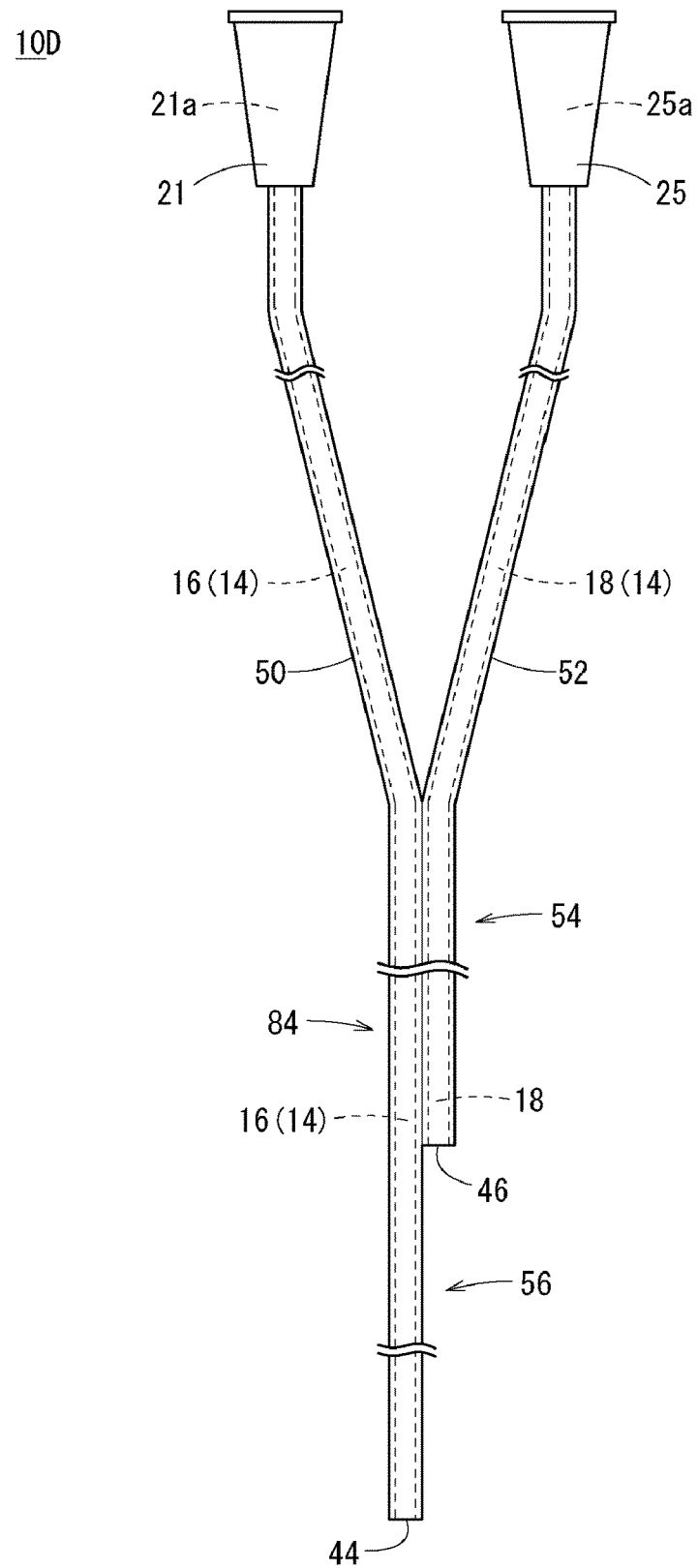
FIG. 10 is a schematic view illustrating a configuration of a catheter according to a first modification.

A catheter 10D according to a first modification illustrated in FIG. 10 is configured such that the hub 28 is not provided, but the first and second catheter portions 50 and 52 are extended to be connected directly to the first and second terminals 21 and 25, respectively. In this case, the catheter 10D has a catheter body 84 in which the first and second catheter portions 50 and 52 are separated in a range from the first and second terminals 21 and 25 to a predetermined position, and the first and second catheter portions 50 and 52 are connected to each other from the predetermined position. The range from the first and second terminals 21 and 25 to the predetermined position corresponds to the first and second ports 20 and 24 described above.

Further, the catheter body 84 also includes the proximal region 54 and the distal region 56 as described hereinbefore. Because the catheter 10D is configured in this manner, the number of parts can be reduced.

Further, the catheter 10D can be easily manufactured by extrusion-molding the first and second catheter portions 50 and 52 simultaneously to be molded as a series of tubular bodies, and then, splitting the first and second catheter portions 50 and 52 in a range from a proximal end to the predetermined position.

Figure 11:
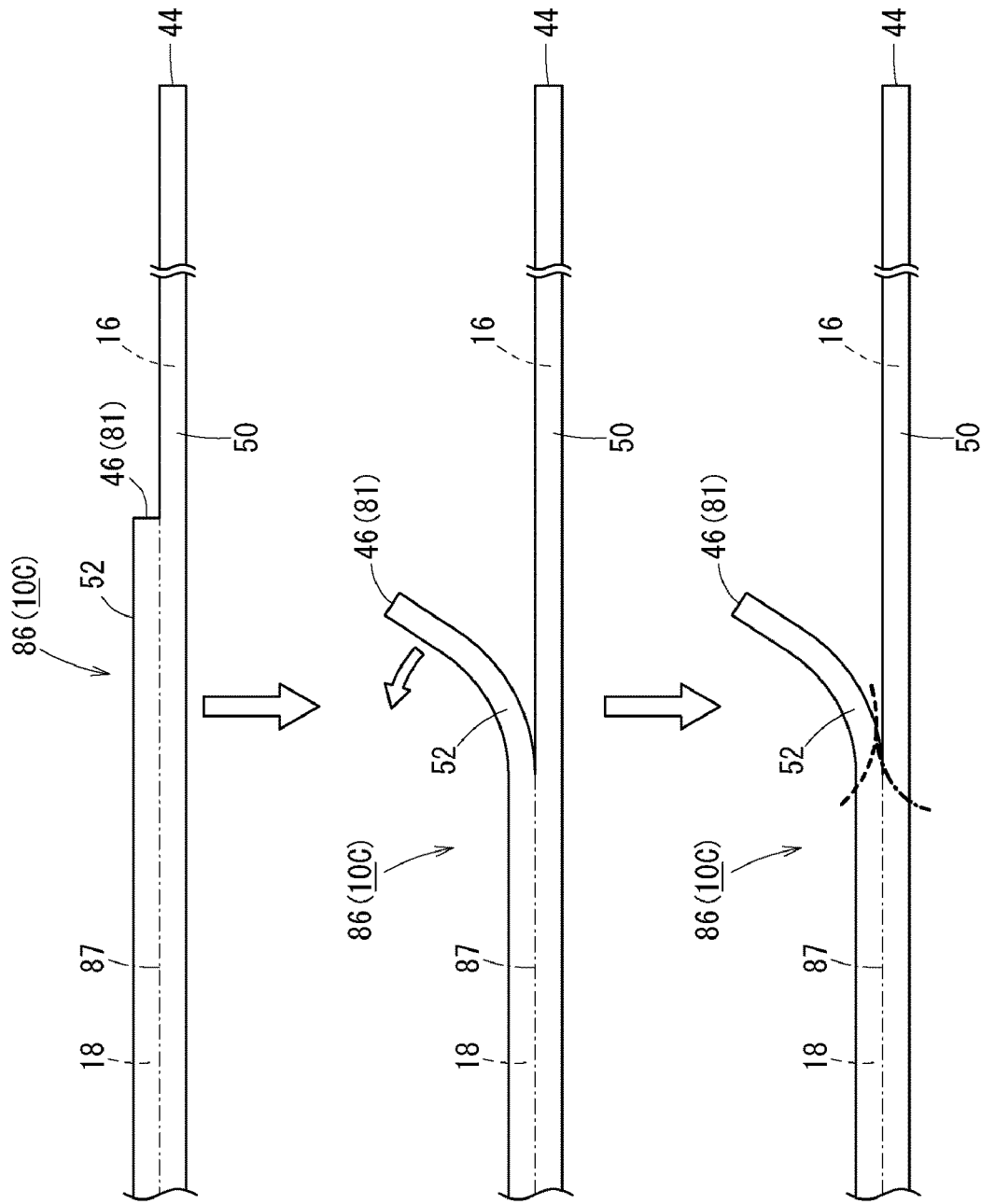
FIG. 11 is an explanatory view for describing separation and trim of a catheter body according to a second modification.

Further, a catheter body 86 according to a second modification illustrated in FIG. 11 is configured such that the first catheter portion 50 and the second catheter portion 52 are separable and can be cut (trimmed). The separation between the first catheter portion 50 and the second catheter portion 52 may be performed at the time of manufacture (before being provided as a product) or performed by a user such as a doctor in accordance with a condition of a patient at the time of using the catheter 10C.

In this case, the catheter body 86 is preferably provided with a fragile portion 87 at a connection portion between the first catheter portion 50 and the second catheter portion 52. The fragile portion 87 is provided so as to extend from the step portion 81 of the catheter body 86 to the proximal end so that the separation between the first catheter portion 50 and the second catheter portion 52 can be promoted along the axial direction.

Figure 12A:
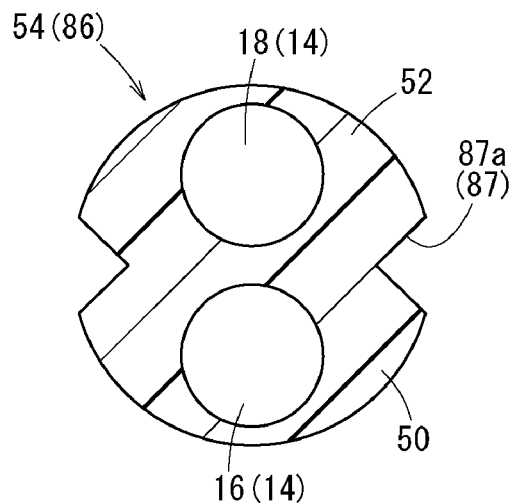
FIG. 12A is a cross-sectional view of the catheter body of FIG. 11.

As such a kind of the fragile portion 87, for example, a concave portion 87a, formed by thinning an outer circumferential surface of the catheter body 86 (a boundary portion between the first catheter portion 50 and the second catheter portion 52) radially inward, can be applied as illustrated in FIG. 12A. In particular, the concave portion 87a is formed in a V-shape in a cross-sectional view orthogonal to the axial direction of the catheter body 86, and thus, can further promote the separation between the first catheter portion 50 and the second catheter portion 52.

The separation between the first catheter portion 50 and the second catheter portion 52 can be performed by mechanically separating the first catheter portion 50 and the second catheter portion 52 by a manufacturing apparatus or a worker (including a user). In addition, for example, the separation may be performed using a medical device such as a cutting cutter and a scalpel (not illustrated).

Further, the trimming of the first catheter portion 50 and the second catheter portion 52 can be obtained by cutting one of parts thereof separated from each other as illustrated in FIG. 11. For example, by cutting the second catheter portion 52 along a broken line in FIG. 11, it is possible to shorten a relative length of the second catheter portion 52 (the proximal region 54) relative to the first catheter portion 50. Further after the separation of the second catheter portion 52 from the first catheter portion 50 is performed as described above, the trimming is performed on a curved portion of the second catheter portion 52 so that it is possible to accurately form a cut end.

Alternatively, the first catheter portion 50 can be also formed to be relatively shorter than the second catheter portion 52 by cutting the first catheter portion 50 along a one-dot chain line in FIG. 11. In this case, a distal end of the second catheter portion 52 is located on the distal side of a distal end of the first catheter portion 50 in the catheter body 86 after trimming, and thus, it can also be considered that the first lumen 16 is present inside the second catheter portion 52 and the second lumen 18 is present in the first catheter portion 50.

Further, the trimming of the first and second catheter portions 50 and 52 is not limited to the above-described method (a pattern of trimming only the distal end of the first catheter portion 50 or a pattern of trimming only the distal end of the second catheter portion 52). For example, both the distal ends of the first and second catheter portions 50 and 52 may be trimmed, and a proximal portion of proximal region (both the first and second catheter portions 50 and 52) may be trimmed. Alternatively, it is also possible to trim both the distal ends of the first and second catheter portions 50 and 52 and the proximal portion of the proximal region 54. Further, it is also possible to adopt a method of trimming the distal end of the first catheter portion 50 and trimming the proximal portion of the proximal region 54, or trimming the distal end of the second catheter portion 52 and trimming the proximal portion of the proximal region 54. Incidentally, the separated portions of the first catheter portion 50 and the second catheter portion 52 may be fixed to each other again after implementation of trimming.

Figure 12B:
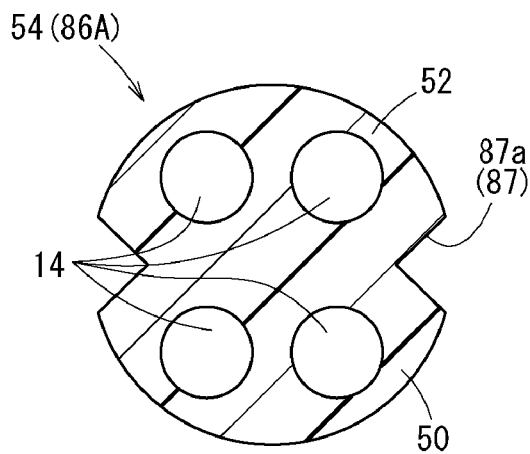
FIG. 12B is a cross-sectional view of a catheter body according to a third modification.
Figure 12C:
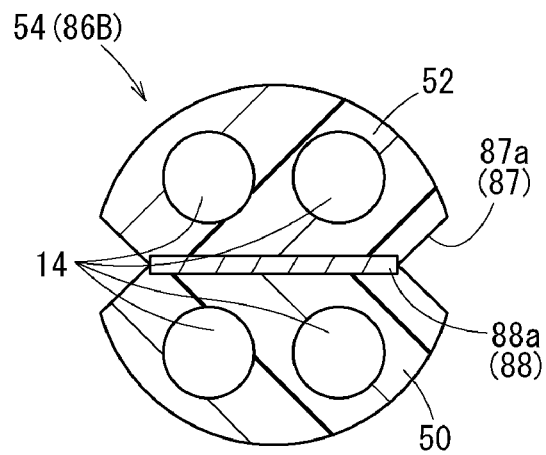
FIG. 12C is a cross-sectional view of a catheter body according to a fourth modification.
Figure 12D:
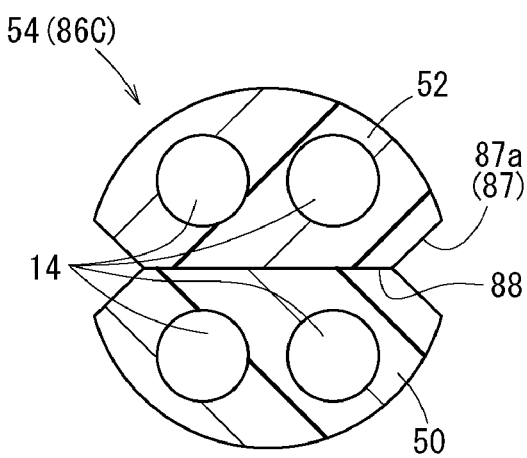
FIG. 12D is a cross-sectional view of a catheter body according to a fifth modification.

Further, a catheter body 86B according to a fourth modification illustrated in FIG. 12C has a damage prevention structure 88 (a hard portion 88a) that suppresses damage of the catheter portion on a non-trimming side during the trimming. For example, the hard portion 88a is formed in a plate shape (a flat layer), and extends between the first catheter portion 50 and the second catheter portion 52 over a predetermined range in the axial direction. As a result, the hard portion 88a can prevent the cutting cutter from damaging the first catheter portion 50, for example, when trimming the second catheter portion 52. Further, for example, as in a catheter body 86C according to a fifth modification illustrated in FIG. 12D, the damage prevention structure 88 can also be realized by forming a predetermined range of the first catheter portion 50 to be harder than the second catheter portion 52.

Further, after the first and second catheter portions 50 and 52 are separated or trimmed, it is preferable to implement an inspection to confirm a function of each lumen of the catheter body 86. Examples of such an inspection include a method of applying a positive pressure or negative pressure from the proximal side in a state where the distal ends of the trimmed first and second lumens 16 and 18 are closed. As a result, it is possible to confirm whether or not an unintended hole or the like is generated in the first catheter portion 50 or the second catheter portion 52.

Further, the trimming on the catheter body 86 also includes changing a shape of the first distal opening 44 or the second distal opening 46 that is provided separately with an opening portion 89 as illustrated in FIGS. 13A and 13B. For example, when the opening portion 89 (lateral hole) connected to the second lumen 18 is formed on a side surface of the second catheter portion 52, the second lumen 18 can discharge the second infusion solution through the opening portion 89 in addition to the second distal opening 46. Incidentally, a plurality of the opening portions 89 may be provided, and the single opening portion 89 may be formed in an elongated hole along the axial direction of the catheter 10C. Further, for example, when the distal end of the second catheter portion 52 is trimmed so as to be connected to the second distal opening 46, the second distal opening 46 can be enlarged in the proximal direction, and the second distal opening 46 can be prevented from being blocked by a blood vessel wall or the like.

Referring back to FIGS. 12B to 12D, each of the catheter bodies 86A to 86C according to the third to fifth modifications illustrated in the drawings has four lumens 14 therein. As these four lumens 14, it is possible to freely arrange long lumens (the first lumen 16 described above) and short lumens (the second lumen 18 described above). For example, it is possible to appropriately adopt a configuration including one long lumen and three short lumens, a configuration including two long lumens and two short lumens, and a configuration including three long lumens and one short lumen.

Further, when the catheter body 86 has three lumens 14, it is possible to adopt a configuration including one long lumen and two short lumens or a configuration including two long lumens and one short lumen although not illustrated.

Further, the catheter bodies 12, 12A, 12B, 72, 80, 84, and 86 (hereinafter collectively referred to as a catheter body 90) of the above catheters 10A to 10D can be manufactured by various manufacturing methods other than the above-described manufacturing method. Next, a manufacturing method of the catheter body 90 will be described with several examples.

For example, in a first manufacturing method illustrated in FIG. 14, the catheter body 90 is manufactured by implementing a molding step of performing extrusion molding to integrally mold a tubular body 91 and a distal region treatment step of trimming a part of the tubular body 91. In this case, in the molding step, a rod-shaped dies, which forms the first lumen 16 and the second lumen 18, is appropriately arranged with respect to an extrusion die that extrudes resin (both the dies are not illustrated), and a molten resin material is extruded from the extrusion die. Each shape of the proximal region 54, the transition region 58, and the distal region 56 of the catheter body 90 described above (cross-sectional shapes of the first and second lumens 16 and 18) can be obtained by changing molding conditions during the extrusion of the tubular body 91. As a result, the double-lumen tubular body 91 surrounding the first and second lumens 16 and 18 is formed as illustrated in an upper drawing of FIG. 14.

In this case, the tubular body 91 has a constant outer diameter (outer diameter of the proximal region 54) in the axial direction based on a shape of the extrusion die (an extrusion port). In the next step, a thick portion on a side where the second lumen 18 is provided, the portion forming the distal region 56 of the tubular body 91, is trimmed (see a lower drawing in FIG. 14). At this time, the location of the transition region 58 is obliquely cut to form the second distal opening 46, and the second lumen 18 can be caused to communicate with the outside.

Figure 15:
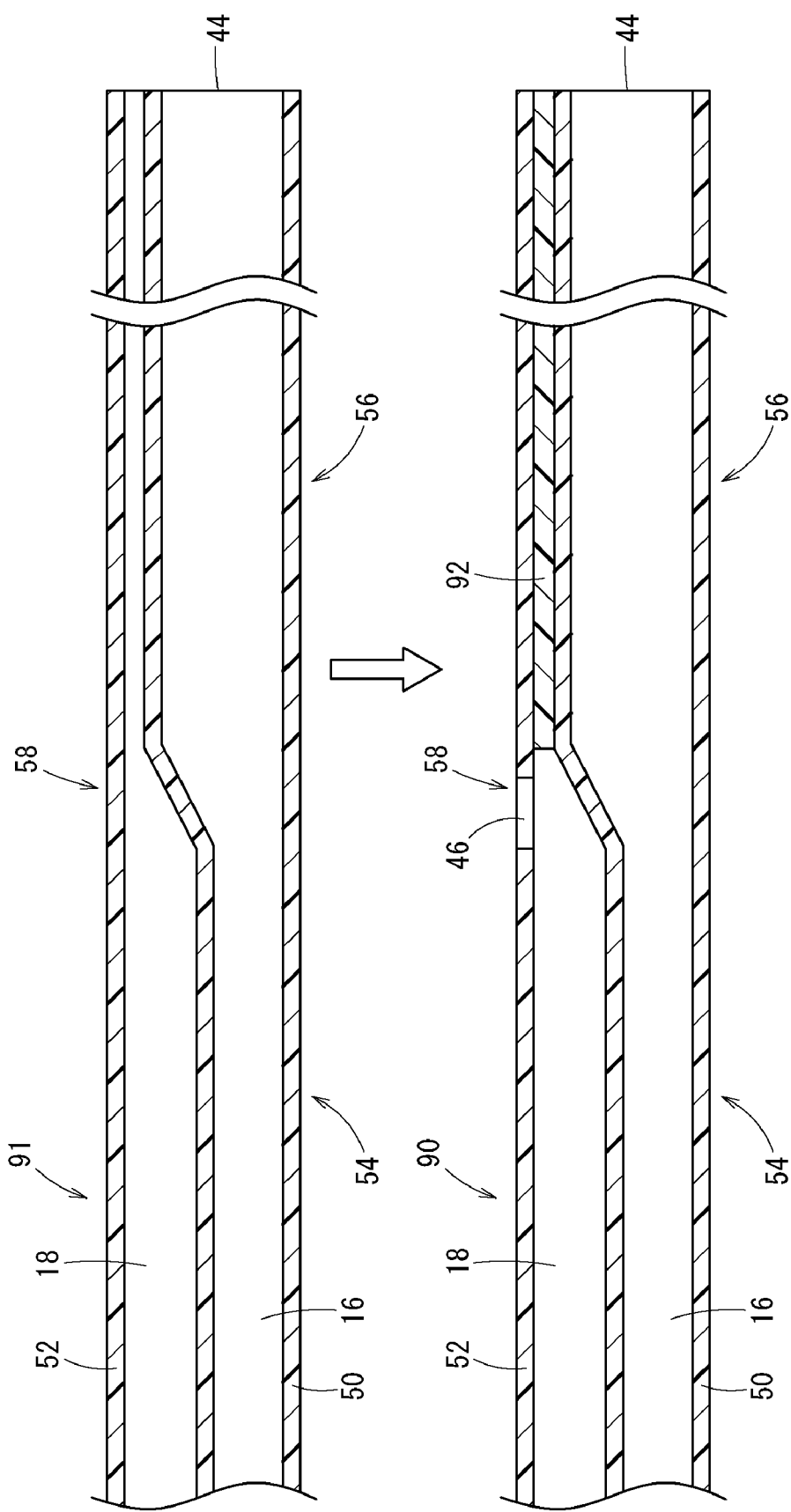
FIG. 15 is a side cross-sectional view for describing a second manufacturing method of the catheter body.

In a second manufacturing method illustrated in FIG. 15, extrusion molding is performed to integrally mold the tubular body 91 (a molding step) similarly to the first manufacturing method. Next, a cutter (not illustrated) is inserted from an outer circumferential surface side of the tubular body 91 to form the second distal opening 46 on the distal side of the second lumen 18 (an opening formation step). Incidentally, the second distal opening 46 illustrated in FIG. 15 is formed in a direction orthogonal to the axial direction of the tubular body 91, but an angle of the second distal opening 46 can be adjusted by changing an insertion angle of the cutter in the opening formation step.

Further, in the second manufacturing method, an appropriate resin material 92 is injected into the second lumen 18 formed in the distal region 56 so as to embed the second lumen 18 of the distal region 56 (a distal region treatment step). In the distal region treatment step, the distal region 56 may be pressurized from the outer circumferential side in order to securely embed the second lumen 18 with the resin material after the injection of the resin material 92, and as a result, the distal region 56 becomes thinner than the proximal region 54. Incidentally, the order of implementing the opening formation step and the distal region treatment step may be reversed in the second manufacturing method. When the distal region treatment step is performed, the second lumen 18 only remains in the proximal region 54 (including the transition region 58) so that a fluid can favorably flow out of the second distal opening 46. Moreover, if the second manufacturing method is adopted, it is also possible to mold the catheter body 12 according to the first embodiment in which the outer diameter does not change along the axial direction.

Figure 16:
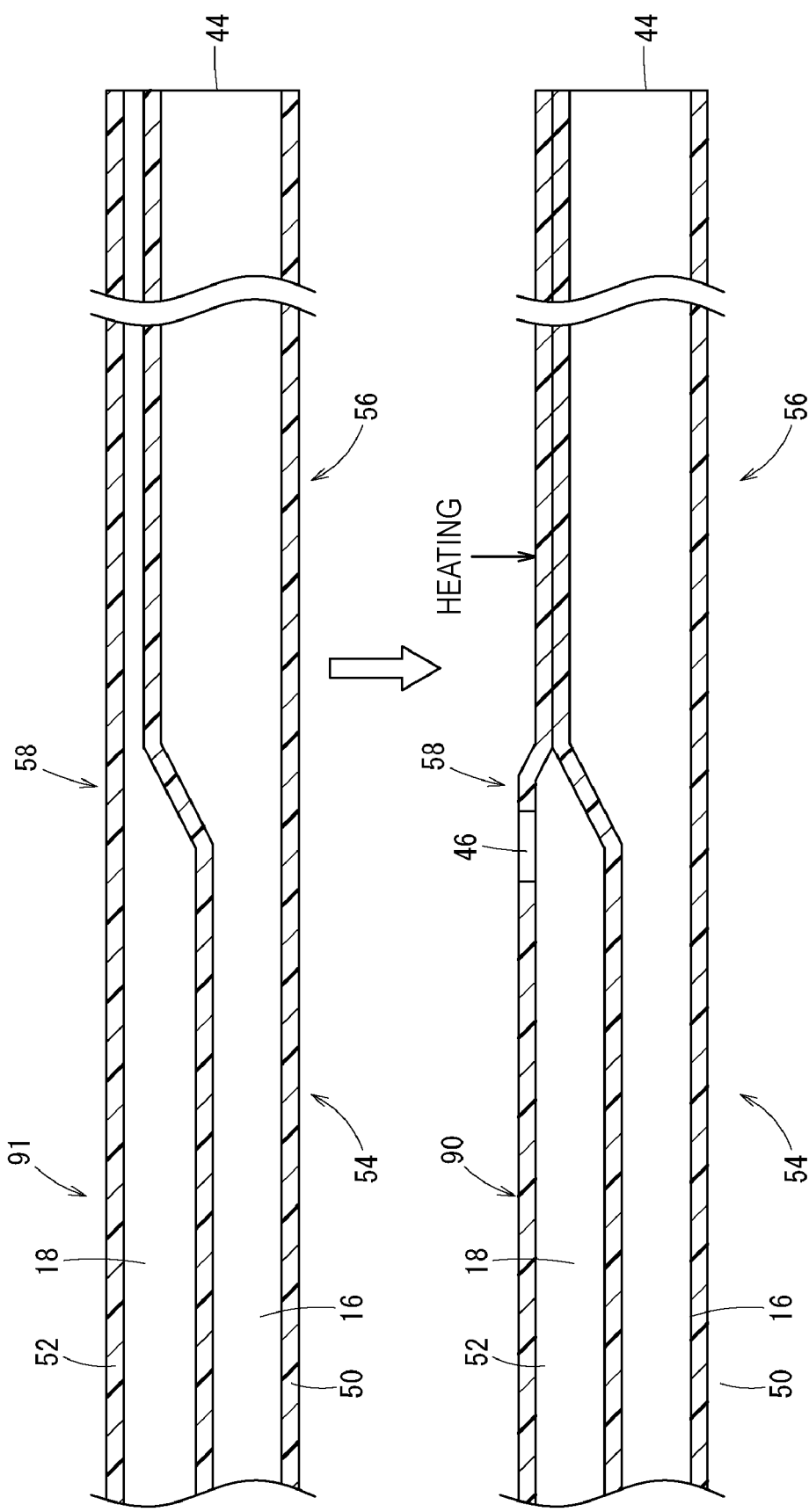
FIG. 16 is a side cross-sectional view for describing a third manufacturing method of the catheter body.

In a third manufacturing method illustrated in FIG. 16, extrusion molding is performed to integrally mold the tubular body 91 (a molding step) similarly to the first manufacturing method. Next, a cutter is inserted from an outer circumferential surface side of the tubular body 91 to form the second distal opening 46 on the distal side of the second lumen 18 (an opening formation step).

Further, in the third manufacturing method, a tubular body on the second lumen 18 side formed in the distal region 56 is heated and crushed to embed the second lumen 18 of the distal region 56 (a distal region treatment step). As a result, the distal region 56 becomes thinner than the proximal region 54. Incidentally, the order of implementing the opening formation step and the distal region treatment step may be reversed even in the third manufacturing method. When the distal region treatment step is performed, the second lumen 18 only remains in the proximal region 54 (including the transition region 58) so that a fluid can favorably flow out of the second distal opening 46.

Figure 17:
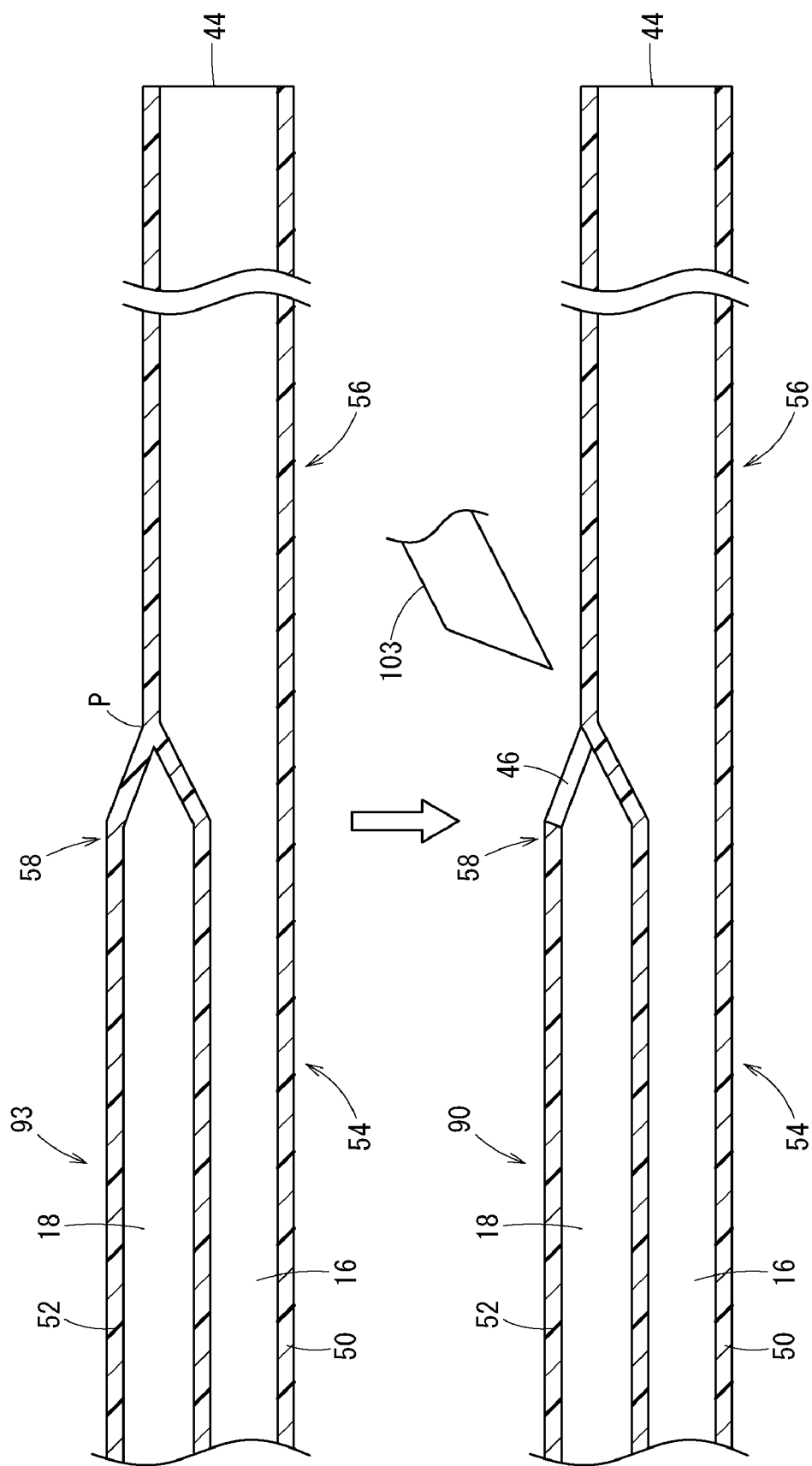
FIG. 17 is a side cross-sectional view for describing a fourth manufacturing method of the catheter body.

In a fourth manufacturing method illustrated in FIG. 17, a molding condition during extrusion molding (a molding step) is changed to mold a tubular body 93 in which the second lumen 18 extends only to the axially intermediate position P in an initial state. As a result, an outer diameter of the proximal region 54 is molded to be larger than an outer diameter of the distal region 56 in the tubular body 93. Further, after the molding step, a cutter 103 is inserted into a portion whose thickness changes on an outer circumferential surface of the tubular body 93 to form the second distal opening 46 on a distal side of the second lumen 18 (an opening formation step). As a result, the second distal opening 46 can be accurately formed to communicate with the second lumen 18, and a fluid can be caused to favorably flow out of the second distal opening 46.

Figure 18:
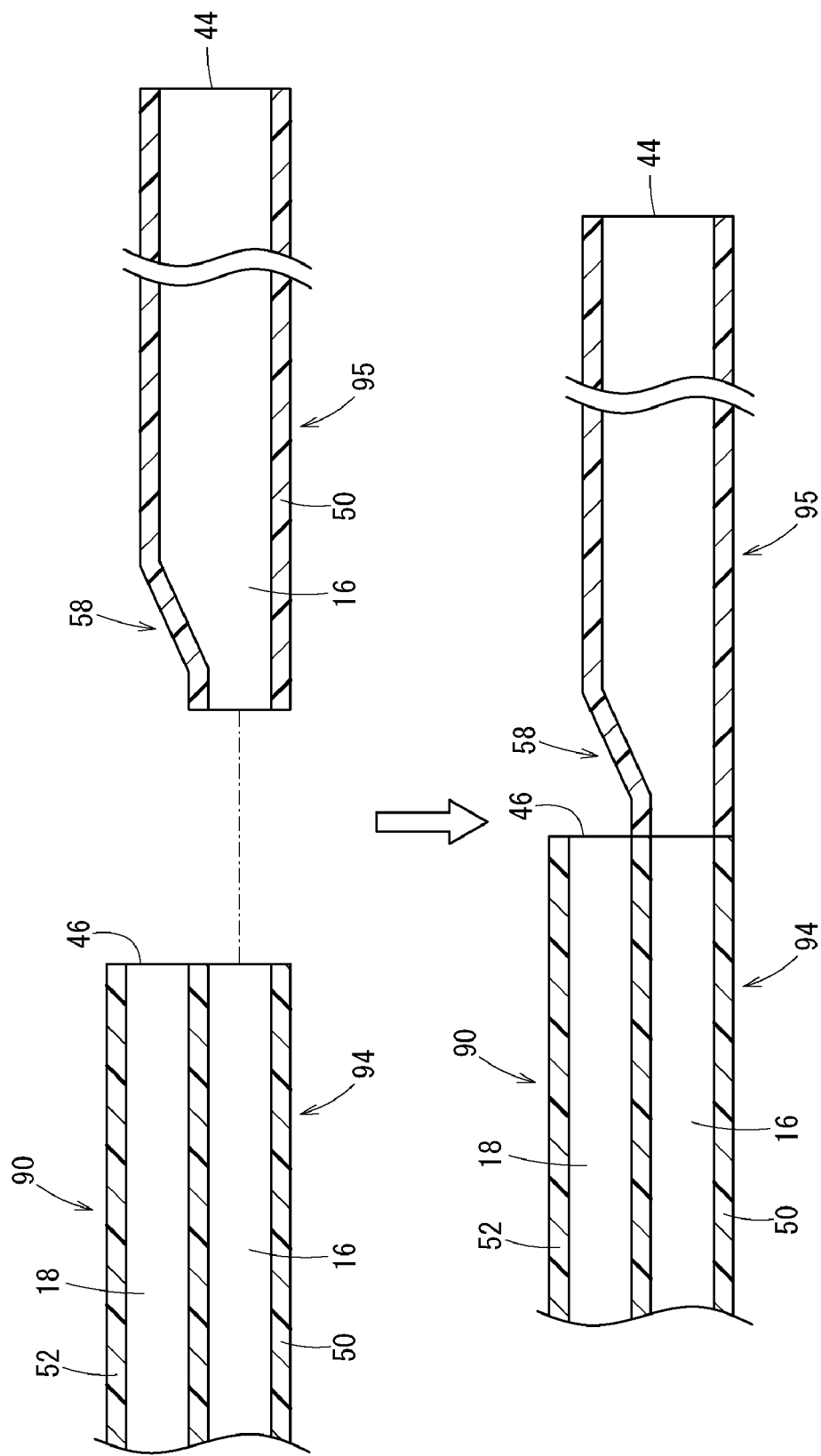
FIG. 18 is a side cross-sectional view for describing a fifth manufacturing method of the catheter body.

In a fifth manufacturing method illustrated in FIG. 18, two types of tubular bodies (a proximal region tubular body 94 and a distal region tubular body 95) are extrusion-molded in a molding step. The proximal region tubular body 94 is formed in a double-lumen member in which the first and second lumens 16 and 18 extend in parallel. On the other hand, the distal region tubular body 95 is formed in a single-lumen member including only the first lumen 16. Further, the transition region 58 whose shape is changed in accordance with a shape of the first lumen 16 of the proximal region tubular body 94 during the molding is formed on one end side of the distal region tubular body 95.

Further, a joining step of joining a distal end of the proximal region tubular body 94 and a proximal end (the transition region 58 side) of the distal region tubular body 95 is performed in the fifth manufacturing method. With this joining step, the first lumen 16 of the proximal region tubular body 94 and the first lumen 16 of the distal region tubular body 95 come into communication with each other, and the second lumen 18 is formed in an open state at an intermediate position of the catheter body 90.

Further, as another example of the fifth manufacturing method, a first tubular body including the first lumen 16 and extending to be long along the axial direction and a second tubular body including the second lumen 18 and extending to be shorter than the first tubular body may be molded in the molding step, and side surfaces of the first tubular body and the second tubular body may be joined to each other in the joining step although not illustrated.

Further, in the first to fifth manufacturing methods, treatment such as applying predetermined coating, impregnating with a solvent, applying hot air, applying a hot fluid, and insertion into a mold may be performed after formation of the catheter body. As a result, a surface of the catheter body is smoothened. In particular, the insertion performance into the blood vessel is enhanced by performing the smoothing treatment on the distal region 56.

Fourth Embodiment

Figure 19:
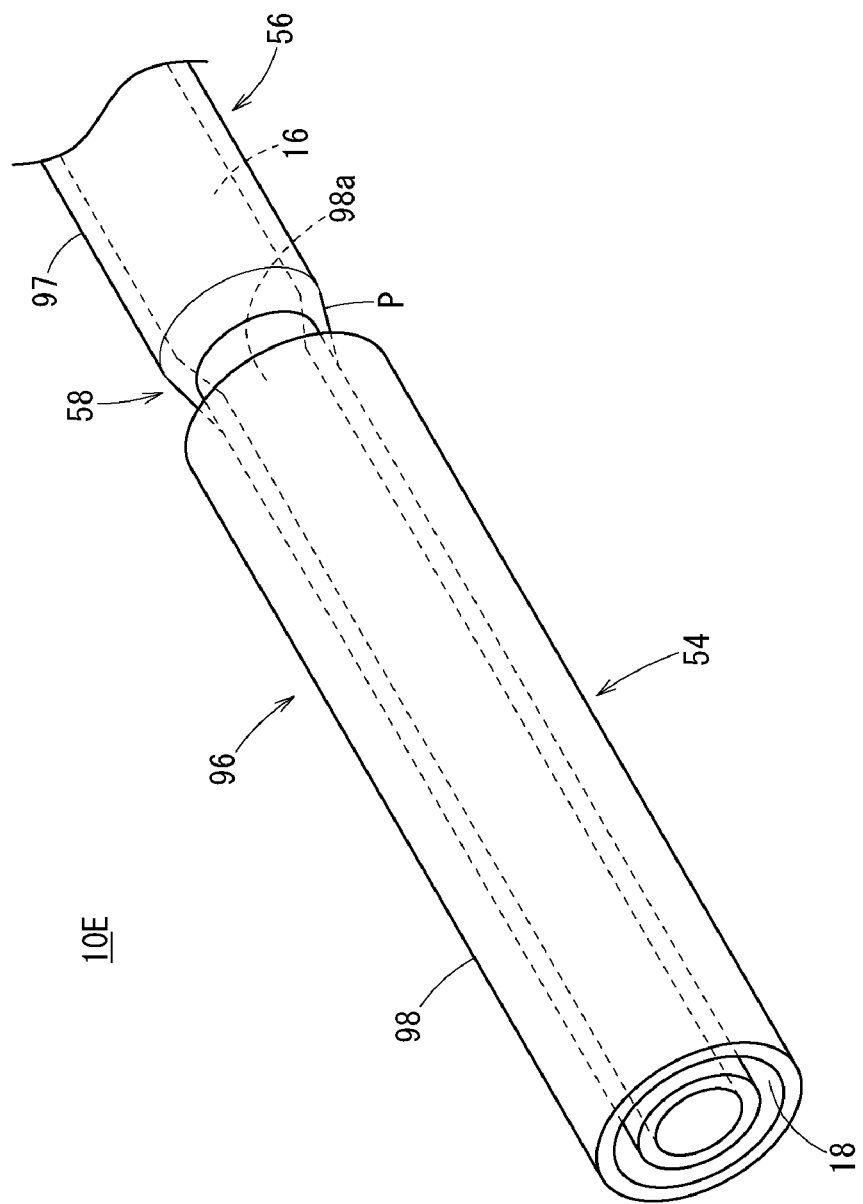
FIG. 19 is a perspective view illustrating a second distal opening of a catheter body of a catheter according to a fourth embodiment and a periphery thereof.

Further, a catheter 10E according to a fourth embodiment of the present invention obtains the same functions as those of the catheter body 12, 12A, 12B, 72, 80, 84, 86, 90 described above by combining two single-lumen-type tubular bodies as illustrated in FIG. 19.

Specifically, a catheter body 96 includes a first tubular body 97 (the first catheter portion 50) having the first lumen 16 and extending to be long along the axial direction. The first tubular body 97 is formed to be thin on a proximal side with respect to the transition region 58 at the axially intermediate position P, and is formed to be thick on a distal side. Further, the first lumen 16 provided in the first tubular body 97 is formed in a circular shape to extend along the axial direction in a cross-sectional view, and is formed such that a diameter of the distal region 56 is large and a diameter of the proximal region 54 is small with the transition region 58 as a reference point (that is, in a relationship of the flow path cross-sectional area Sp<Sd). Alternatively, the first tubular body 97 may be formed to have a constant outer diameter and a constant flow path cross-sectional area of the first lumen 16 (that is, the flow path cross-sectional area Sp=Sd) similarly to the third embodiment.

Further, a second tubular body 98 (the second catheter portion 52), which includes the second lumen 18 and is shorter than the first tubular body 97, is formed in the catheter body 96 in a manufacturing process before completion. An axial length of the second tubular body 98 substantially coincides with an axial length from the proximal end of the first tubular body 97 to the transition region 58. Further, a diameter of the second lumen 18 of the second tubular body 98 is larger than the outer diameter of the proximal region 54 of the first tubular body 97.

The catheter body 96 becomes a member that can be integrally inserted into a patient by inserting the proximal region 54 of the first tubular body 97 into the second lumen 18 of the second tubular body 98. Further, in an assembled state, a gap is generated between an outer circumferential surface of the first tubular body 97 and an inner circumferential surface of the second tubular body 98 due to the second lumen 18, and this gap communicates with a distal opening 98a of the second tubular body 98 (an opening portion between the outer circumferential surface of the first tubular body 97 and the inner circumferential surface of the second tubular body 98). That is, the catheter body 96 can cause the first infusion solution to flow through the first lumen 16 and flow out of the first distal opening 44 as described above. On the other hand, the second infusion solution can be made to flow through the second lumen 18 (the gap between the outer circumferential surface of the first tubular body 97 and the inner circumferential surface of the second tubular body 98) and flow out of the distal opening 98a.

Further, the catheter 10E according to the fourth embodiment can also be provided as a catheter set including the first tubular body 97 and the second tubular body 98 in the state before the catheter body 96 is assembled as illustrated in FIG. 20. For example, the catheter set is configured to include the first tubular body 97 fixedly held by a first hub 99a and the second tubular body 98 fixedly held by a second hub 99b, and forms the catheter body 96 when being assembled by the user at the time of use.

At the time of assembling the catheter body 96, it is possible to easily perform the assembling by inserting the first tubular body 97 from a proximal side of the second hub 99b to send the first tubular body 97 from the distal end of the second tubular body 98. Incidentally, the catheter body 96 can be integrated more reliably by locking a proximal end of the second hub 99*b* and a distal end of the first hub 99*a* with each other using a locking mechanism at the time of assembling.

Incidentally, the present invention is not limited to the above-described embodiments, and various modifications are possible in accordance with a gist of the invention.

What is claimed is:

1. A method of using a catheter, the method comprising: providing the catheter, which comprises:
   a catheter body defining:
      a first catheter portion defining a first lumen communicating with a first distal opening, and
      a second catheter portion defining a second lumen communicating with a second distal opening,
      wherein the second distal opening positioned proximal of the first distal opening,
      wherein a flow path cross-sectional area of the first lumen in at least a part of a distal region of the catheter body that is distal of the second distal opening is larger than a flow path cross-sectional area of the first lumen in a proximal region of the catheter body that is proximal of the second distal opening,
      wherein the catheter body includes a tubular body having an outer circumferential surface that is recessed radially inward to form a groove portion, and
      wherein a first part of the groove portion is covered by a covering member and a second part of the groove portion is exposed from the covering member to form the second distal opening; and
   positioning the catheter in a blood vessel of an individual such that the second distal opening is located at a position in an arm of the individual, and the first distal opening is located at a position at or near a central vein of the individual;
   infusing a first infusion solution into the blood vessel at the position at or near the central vein of the individual via the first distal opening; and
   infusing a second infusion solution into the blood vessel at the position in the arm of the individual via the second distal opening.

2. The method of using a catheter according to claim 1, wherein:
   a first medical bag storing the first infusion solution is fluidly coupled to the first lumen through a first port; and
   a second medical bag storing the second infusion solution is fluidly coupled to the second lumen through a second port.

3. The method of using a catheter according to claim 1, wherein:
   the groove portion causes the second infusion solution to infuse from the second distal opening at an angle relative to an axial direction of the catheter body.

4. The method of using a catheter according to claim 1, wherein:
   an outer diameter of the catheter body in the proximal region is substantially equal to an outer diameter of the catheter body in the distal region.

5. The method of using a catheter according to claim 1, wherein:
   an outer diameter of the catheter body in the proximal region is larger than an outer diameter of the catheter body in the distal region.

6. The method of using a catheter according to claim 1, wherein:
   a cross-sectional shape of the first lumen in a cross-section orthogonal to an axial direction of the first lumen is a non-circular shape in the proximal region and is a circular shape in the distal region.

7. The method of using a catheter according to claim 6, wherein:
   the non-circular shape is a crescent shape.

8. The method of using a catheter according to claim 1, wherein:
   at least a portion of the distal region of the catheter body is flexible.

9. The method of using a catheter according to claim 1, wherein:
   the first catheter portion and the second catheter portion are separable; and
   the method further comprises, before positioning the catheter in a blood vessel, separating part of the second catheter portion from the first catheter portion and trimming the second catheter portion.

10. The method of using a catheter according to claim 9, wherein:
   a fragile portion that allows for separation is located at a boundary between the first catheter portion and the second catheter portion.

11. The method of using a catheter according to claim 1, wherein:
   a hardness of the second catheter portion is greater than a hardness of the first catheter portion.

12. The method of using a catheter according to claim 1, wherein:
   the covering member comprises a sheet of resin.

* * * * *